United States Patent [19]
Tanzer et al.

[11] Patent Number: 5,433,715
[45] Date of Patent: Jul. 18, 1995

[54] ABSORBENT ARTICLE WHICH INCLUDES SUPERABSORBENT MATERIAL LOCATED IN DISCRETE POCKETS HAVING WATER-SENSITIVE AND WATER-INSENSITIVE CONTAINMENT STRUCTURES

[75] Inventors: Richard W. Tanzer, Neenah, Wis.; Frank P. Abuto, Alpharetta, Ga.; Stanley R. Kellenberger, Appleton, Wis.; Daniel R. Laux, Appleton, Wis.; Brian K. Nortman, Appleton, Wis.; William S. Pomplun, Neenah, Wis.; Carl G. Rippl; Mark L. Robinson, both of Appleton, Wis.; Lorry F. Sallee, Pine River, Wis.; Wen Z. Schroeder, Appleton, Wis.; Sandra M. Yarbrough, Menasha, Wis.; David L. Zenker, Neenah, Wis.

[73] Assignee: Kimberly-Clark Corporation, Neenah, Wis.

[21] Appl. No.: 145,925

[22] Filed: Oct. 29, 1993

[51] Int. Cl.⁶ .................. A61F 13/15; A61F 13/20
[52] U.S. Cl. .................. 604/368; 604/358; 604/367; 604/372; 604/378; 604/385.1
[58] Field of Search ............... 604/358, 364, 365, 367, 604/368, 372, 378, 382, 385.1

[56] References Cited

U.S. PATENT DOCUMENTS

| | | |
|---|---|---|
| 2,331,271 | 10/1943 | Gilchrist . |
| 2,897,109 | 7/1959 | Voigtman . |
| 3,498,296 | 3/1970 | Gallagher ........................... 604/378 |
| 3,676,242 | 7/1972 | Prentice . |
| 4,055,180 | 10/1977 | Karami ............................... 604/368 |
| 4,224,366 | 9/1980 | McCabe, Jr. . |
| 4,327,728 | 5/1982 | Elias . |
| 4,333,462 | 6/1982 | Holtman et al. . |
| 4,360,021 | 11/1982 | Stima . |
| 4,381,783 | 5/1983 | Elias . |
| 4,413,996 | 11/1983 | Taylor . |
| 4,414,255 | 11/1983 | Tokuyama et al. . |
| 4,429,001 | 1/1984 | Kolpin et al. . |
| 4,574,021 | 3/1986 | Endres et al. . |
| 4,578,066 | 3/1986 | O'Connor . |
| 4,592,751 | 6/1986 | Gegelys . |

(List continued on next page.)

FOREIGN PATENT DOCUMENTS

| | | |
|---|---|---|
| 1085102 | 9/1980 | Canada . |
| 1134126 | 10/1982 | Canada . |
| 1241504 | 9/1988 | Canada . |
| 1260249 | 9/1989 | Canada . |
| 0222585 | 5/1987 | European Pat. Off. . |
| 0223487A2 | 5/1987 | European Pat. Off. . |
| 022835381 | 7/1987 | European Pat. Off. . |
| 0339461B1 | 11/1989 | European Pat. Off. . |
| 2112828 | 7/1983 | United Kingdom . |
| 2113731 | 8/1983 | United Kingdom . |
| 2151272 | 7/1985 | United Kingdom . |
| WO89/01325 | 2/1989 | WIPO . |

Primary Examiner—Randall L. Green
Assistant Examiner—P. Zuttarelli
Attorney, Agent, or Firm—Paul Yee

[57] ABSTRACT

An absorbent article comprises a first, liquid-permeable carrier layer and at least a second carrier layer. A water sensitive attaching mechanism secures together the carrier layers to provide substantially attached zones and substantially unattached zones thereof. The substantially unattached zones provide a plurality of pocket regions, and a high absorbency material is located within the pocket regions to provide an absorbent laminate. A secondary attaching mechanism secures together the carrier layers along selected secondary attachment regions and provides a substantially water-insensitive connection therebetween. The secondary attachment regions are substantially restricted to locations spaced from the pocket regions.

27 Claims, 11 Drawing Sheets

OTHER PUBLICATIONS

| | | |
|---|---|---|
| 4,604,313 | 8/1986 | McFarland et al. . |
| 4,655,757 | 4/1987 | McFarland et al. . |
| 4,670,011 | 6/1987 | Mesek . |
| 4,676,785 | 6/1987 | Battista . |
| 4,715,918 | 12/1987 | Lang . |
| 4,724,114 | 2/1988 | McFarland et al. . |
| 4,741,941 | 5/1988 | Englebert et al. . |
| 4,781,711 | 11/1988 | Houghton et al. ............ 604/367 |
| 4,790,839 | 12/1988 | Ahr ................................ 604/367 |
| 4,840,692 | 6/1989 | Kamstrup-Larsen . |
| 4,886,509 | 12/1989 | Mattsson . |
| 4,892,535 | 1/1990 | Bjornberg et al. . |
| 4,960,477 | 10/1990 | Mesek ............................ 604/379 |
| 4,988,344 | 1/1991 | Reising et al. . |
| 4,994,053 | 2/1991 | Lang . |
| 5,030,314 | 7/1991 | Lang . |
| 5,072,687 | 12/1991 | Mitchell et al. . |
| 5,118,376 | 6/1992 | Pigneul et al. . |
| 5,149,335 | 9/1992 | Kellenberger et al. . |
| 5,175,046 | 12/1992 | Nguyen . |
| 5,196,470 | 3/1993 | Anderson et al. . |

ABSORBENT ARTICLE WHICH INCLUDES SUPERABSORBENT MATERIAL LOCATED IN DISCRETE POCKETS HAVING WATER-SENSITIVE AND WATER-INSENSITIVE CONTAINMENT STRUCTURES

TECHNICAL FIELD

This invention relates to absorbent articles, particularly absorbent personal care products. More particularly, the invention relates to disposable garments which include discrete pockets of superabsorbent polymer material held between a pair of carrier sheets.

BACKGROUND OF THE INVENTION

Absorbent articles, such as disposable diapers, have comprised an absorbent pad assembly having an absorbent pad and pockets for retaining a hydrocolloid material in association with the pad. For example, see U.S. Pat. No. 4,055,180 issued Oct. 25, 1977 to H. Karami, and U.S. Pat. No. 4,360,021 issued Nov. 23, 1982 to J. Stima.

Absorbent articles have also comprised an absorbent layer having at least one pocket containing a uniform admixture of discrete superabsorbent particles and discrete introfying particles. For example, see U.S. Pat. No. 4,327,728 issued May 4, 1982 to R. Elias, and U.S. Pat. No. 4,381,783 issued May 3, 1983 to R. Elias.

Other absorbent articles have included a quantity of highly liquid-sorbent superabsorbent material provided in discrete spaced-apart regions between upper and lower fibrous webs of a diaper batt, with a network of densified wicking embossments and at least one integral densified wicking layer provided for promoting efficient wicking and transport of liquid within the absorbent structure. See, for example, U.S. Pat. No. 4,960,477 issued Oct. 2, 1990 to F. Mesek.

Conventional absorbent articles, such as those described above, have not provided adequate performance. The employed quantities of superabsorbent material have not been efficiently utilized and the containment of the superabsorbent material during the use cycle of the article has been inadequate. The uptake rate of absorbed liquids has been insufficient, and the absorbent articles have exhibited excessive leakage.

BRIEF DESCRIPTION OF THE INVENTION

Generally stated, the present invention provides a distinctive absorbent article comprising a first, liquid-permeable carrier layer and at least a second carrier layer. A water-sensitive attaching means secures together the carrier layers to provide substantially attached zones and substantially unattached zones thereof. The substantially unattached zones provide a plurality of pocket regions, and a high absorbency material is located within the pocket regions to provide an absorbent laminate. A secondary attaching means secures together the carrier layers along selected secondary attachment regions and provides a substantially water-insensitive connection therebetween. The secondary attachment regions are substantially restricted to locations spaced from the pocket regions.

The various aspects of the absorbent article of the invention can provide an absorbent structure which more securely locates and contains the high-absorbency material in a selected array of pockets when the article is dry. When the article becomes wetted, the absorbent structure of the invention can better maintain the location of the high-absorbency material while accommodating the increased volume of the swollen material. In addition, the swollen absorbent gel material is less liable to escape the confines of the absorbent laminate. At the same time, the water-sensitivity of the attaching means can help maintain interstitial channels between the individual pocket regions to facilitate the flow of liquid to each of the pocket regions. The quantity of high-absorbency material contained in the pocket regions of the absorbent structure can be more efficiently utilized, and the absorption characteristics of the structure can be improved. As a result, the absorbent article can be configured with a thinner structure which is capable of absorbing larger amounts of liquid and exhibits reduced leakage. The thinner structure can in turn provide improved fit and comfort on the wearer.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The absorbent structures of the present invention will be described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for reuse. The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as adult incontinence garments, sanitary napkins, children's training pants, bed pads and the like.

Figure 1:
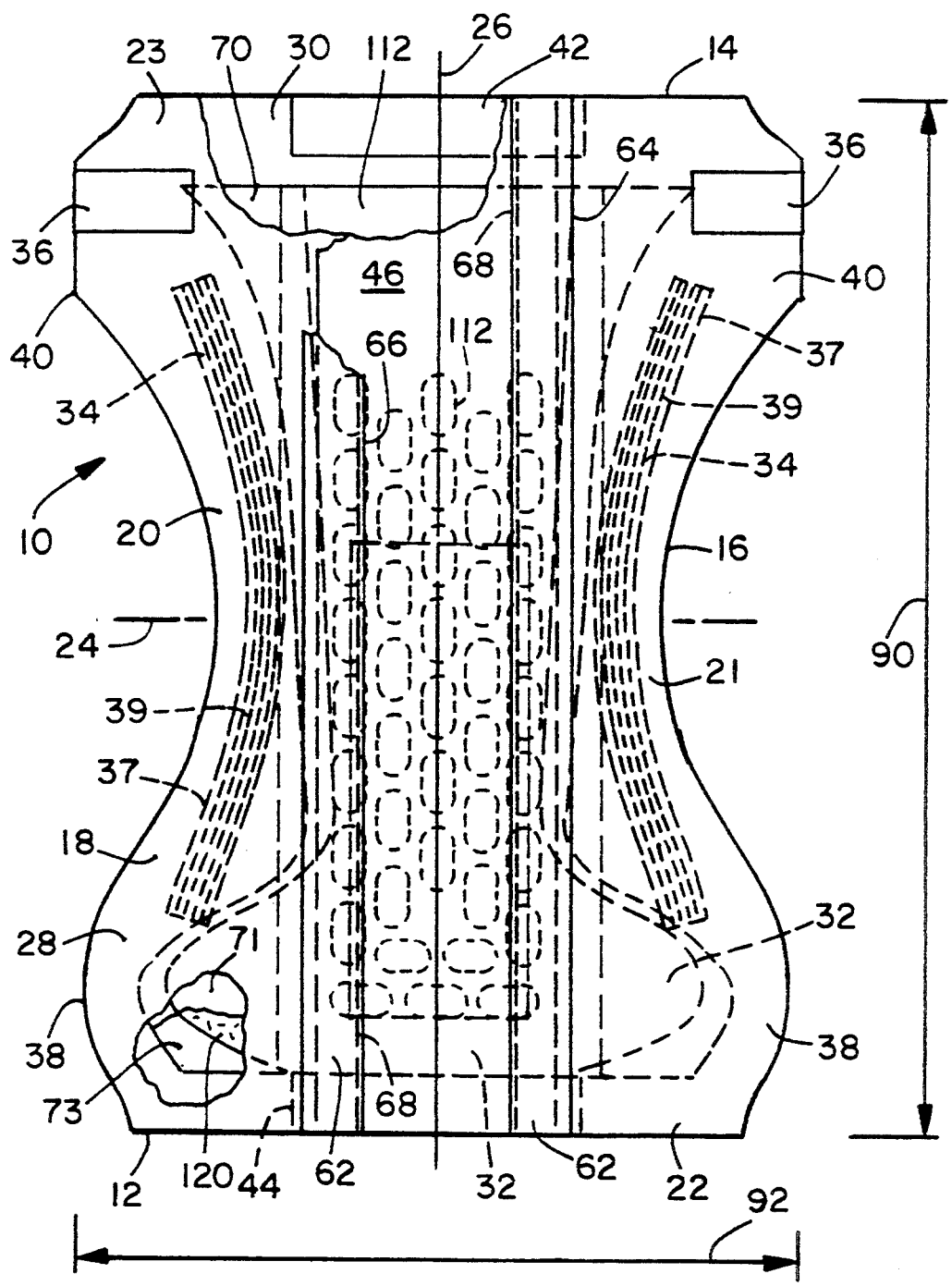
FIG. 1 representatively shows a partially cut-away, top plan view of a fully extended article of the invention.
Figure 2:
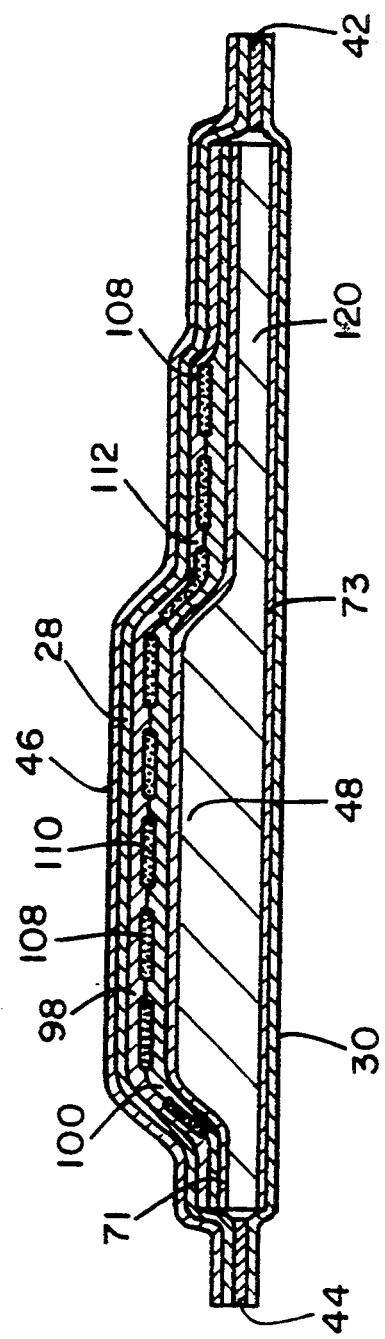
FIG. 2 representatively shows a length-wise, cross-sectional, side view of the article of the invention illustrated in FIG. 1.

With reference to FIGS. 1 and 2, an absorbent article, such as diaper 10, is representatively shown in its extended, flat-out condition with all elastic contractions and gathers removed. The absorbent article can have a distinctive absorbent structure, as representatively shown in FIGS. 5, 6 and 7. The absorbent structure includes a first, liquid permeable carrier layer 98 and at least a second carrier layer 100. A water-sensitive attaching means, such as a water-sensitive adhesive 102, secures together carrier layers 98 and 100 to provide substantially attached zones 104 and a multiplicity of substantially unattached zones 106 thereof. The substantially unattached zones 106 provide a plurality of pocket regions 108, and a high absorbency material, such as particles of superabsorbent material 110, are located within pocket regions 108 to provide an absorbent laminate 112.

In the various configurations of the invention, the attaching means employed to construct absorbent laminate 112 is strong enough to operably maintain the integrity of the laminate when the laminate is substantially dry. In addition, the attaching means has sufficient strength to generally maintain the integrity of the laminate when the carrier sheets have been substantially wetted with an aqueous liquid, such as urine. The holding strength of the attaching means, however, is sufficiently low enough to substantially avoid excessive restriction of the swelling of the high absorbency material when the high absorbency material is wetted to substantial saturation. Additionally, the strength of the attaching means is sufficiently low enough to allow a separation of carrier layer 98 from carrier layer 100 under the forces of expansion generated by high absorbency material as the high absorbency material absorbs the aqueous liquid. In suitable cooperation with the strength of the attaching means, the carrier layers are configured to have a burst strength which is greater than the attachment strength of the attaching means.

The selected holding strength of the attaching means and the selected, controlled separation can allow the high absorbency material to effectively and efficiently swell in volume during the absorption of liquid while substantially avoiding a bursting of either or both of the carrier layers.

In FIG. 1, portions of the structure are partially cut away to more clearly show the construction of diaper 10, and the side of the diaper which contacts the wearer is facing the viewer. The shown embodiment of diaper 10 has an intermediate crotch region 16 which interconnects the front and rear waistband regions 12 and 14. The outer edges of the diaper define a periphery 18 in which the longitudinally extending side edge margins are designated 20 and the laterally extending end edge margins are designated 22. Preferably, the side edges are curvilinear and contoured to define leg openings for the diaper. The end edges are shown as straight, but optionally, may be curvilinear. The diaper additionally has a transverse center line 24 and a longitudinal center line 26.

Diaper 10 can include a liquid permeable topsheet 28; a substantially liquid impermeable backsheet 30; an absorbent body, such as an absorbent structure 32, positioned between the topsheet and backsheet; leg elastic members 34; and waist elastic members 42 and 44. Topsheet 28, backsheet 30, absorbent structure 32, and elastic members 34, 42 and 44 may be assembled in a variety of well-known diaper configurations.

Figure 4:
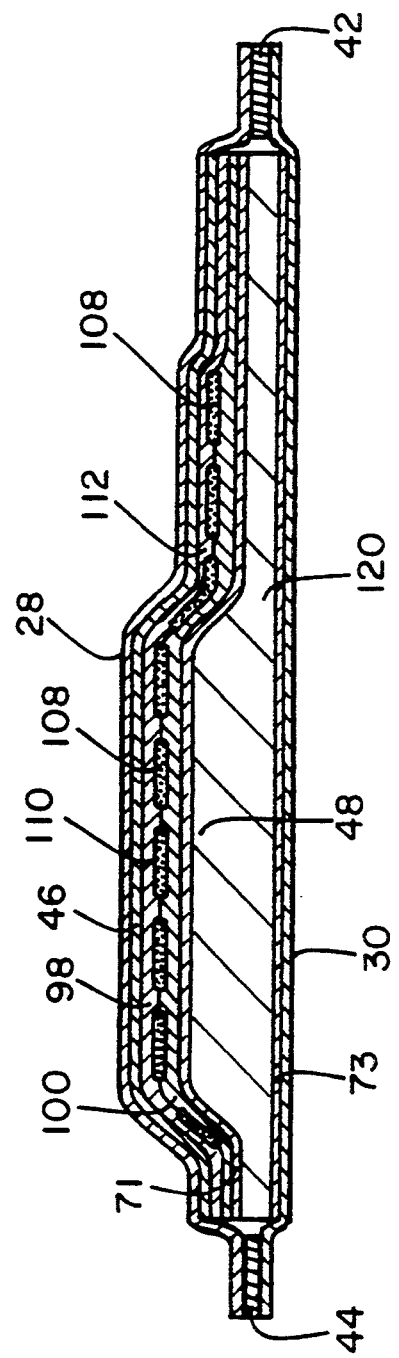
FIG. 4 illustrates a length-wise, cross-sectional, side view of an embodiment of a representative article of the invention having a surge layer on the outer side surface of the topsheet.
Figure 5:
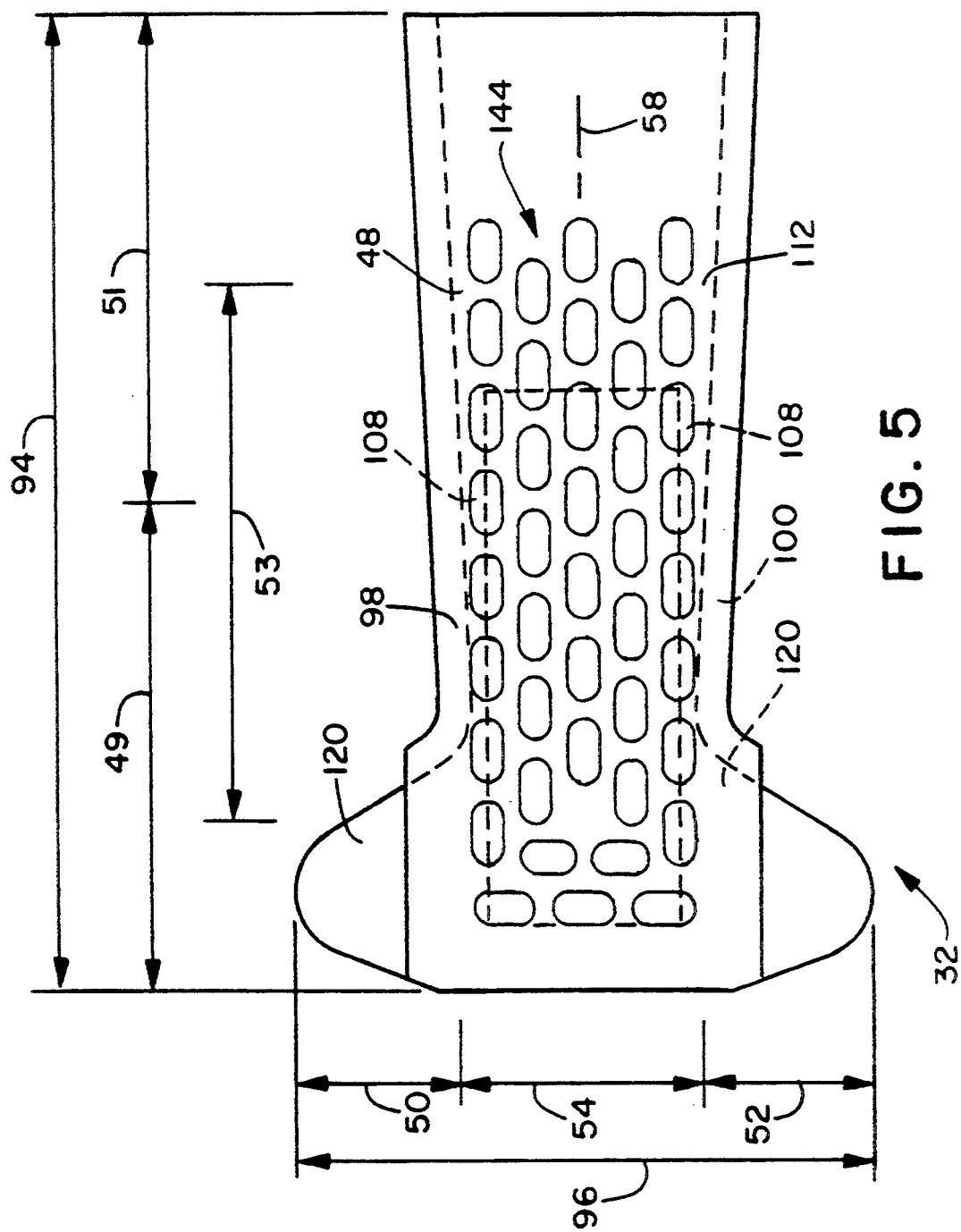
FIG. 5 representatively shows a top view of an absorbent structure of the invention having an absorbent laminate located on a bodyside surface of a supplemental absorbent body provided by a selected distribution layer.
Figure 8:
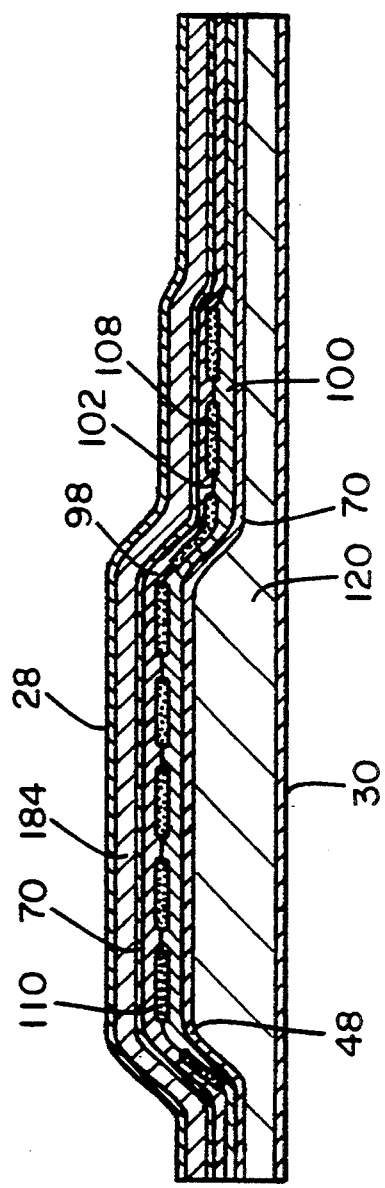
FIG. 8 representatively shows a cross-sectional, side view of an absorbent structure of the invention having a distribution layer positioned on a bodyside surface of an absorbent laminate.

With reference to FIGS. 4 and 5, the various aspects of the absorbent article of the invention can comprise an absorbent structure 32 which includes a retention portion 48 having a primary absorbent portion, such as absorbent laminate 112, for storing and holding absorbed liquids, such as urine. The retention portion can also include a supplemental absorbent, such as an outer side distribution layer 120, and in particular aspects of the invention, the supplemental absorbent can alternatively or additionally include a bodyside distribution layer 184 (FIG. 8).

The various aspects of the invention can also provide an absorbent article having a surge management portion 46, which may be located on a bodyside surface of topsheet 28 (FIG. 2), or alternatively, may be located on an opposite, outer side surface of the topsheet which faces toward backsheet 30 (FIG. 4). In an optional arrangement of the invention, the surge management portion may be cooperatively arranged with a multi-piece topsheet. Such a topsheet configuration can, for example, include two, individual topsheet sections which are laterally spaced-apart from each other along the diaper cross-direction, and an intermediate surge management portion which is operatively connected to bridge therebetween. The surge management portion thereby provides the medial section of the topsheet composite assembly.

Absorbent article structures suitable for use with the present invention are described in U.S. patent application Ser. No. 07/757,778 of D. Proxmire et al., filed Sep. 11, 1991, and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932), now U.S. Pat. No. 5,192,606 issued Mar. 9, 1993, the disclosure of which is hereby incorporated by reference to the extent that it is consistent (not contradictory) with the present specification. Other absorbent article structures suitable for use with the present invention are described in U.S. patent application Ser. No. 07/757,760; "THIN ABSORBENT ARTICLE HAVING RAPID UPTAKE OF LIQUID"; of W. Hanson et al. (Attorney Docket No. 9922), the disclosure of which is hereby incorporated by reference to the extent that it is consistent herewith.

Figure 3:
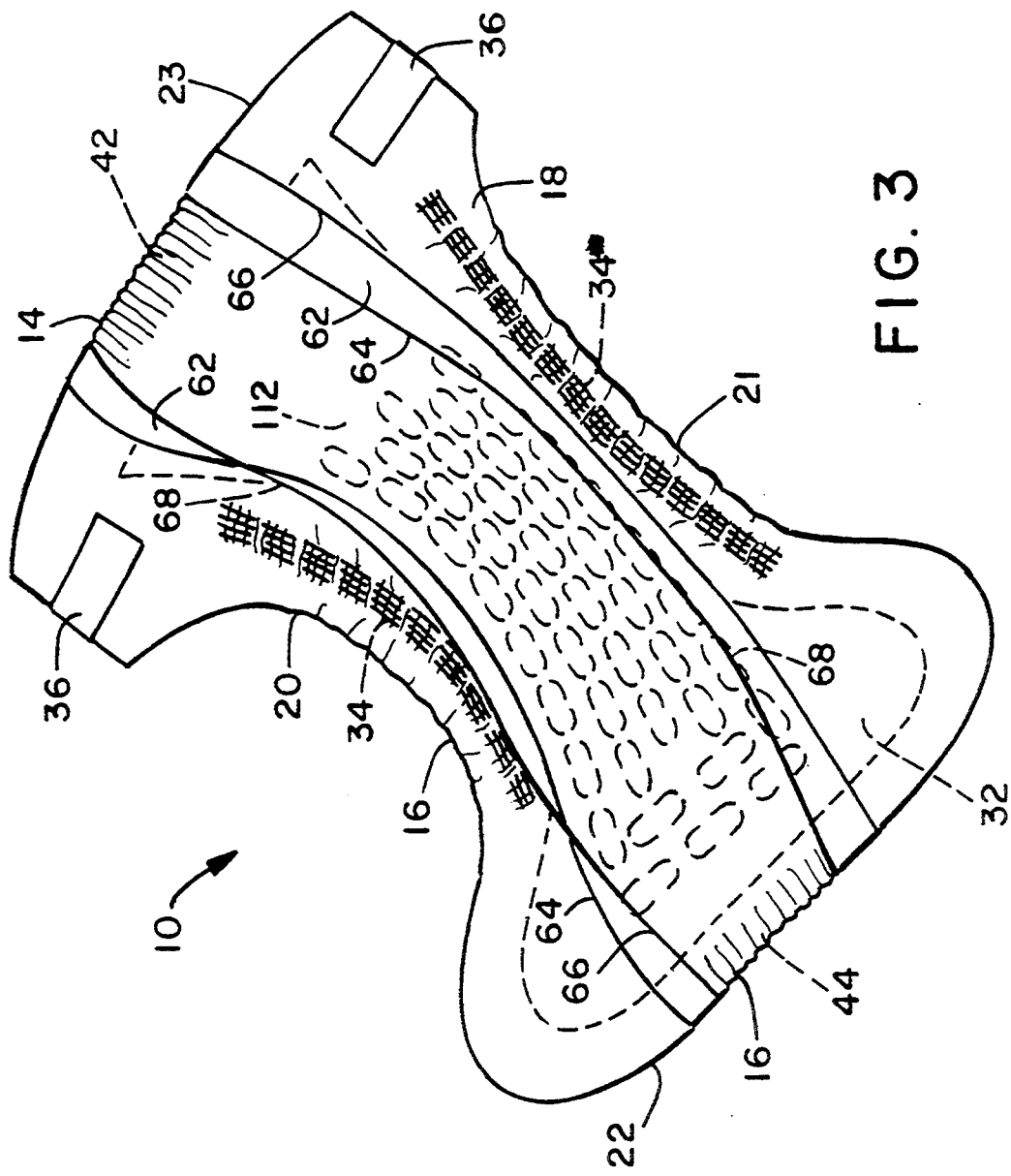
FIG. 3 representatively shows a perspective view of an article of the invention wherein the various elastics have contracted to gather the elasticized sections thereof.

In the embodiment of diaper 10 representatively shown in FIGS. 1–3, topsheet 28 and backsheet 30 are generally coextensive and have length and width dimensions which are generally larger than the corresponding dimensions of absorbent structure 32. Topsheet 28 is associated with and superimposed on backsheet 30, thereby defining the periphery 18 of diaper 10. The periphery delimits the outer perimeter or the edges of the diaper 10, and in the illustrated embodiment, comprises end edges 22 and contoured longitudinal edges 20. The diaper 10 has front and back waistband regions 12 and 14, respectively extending from the laterally extending end edges 22 of diaper periphery 18 toward the transverse center line 24 of the diaper along a distance of from about 2 percent to about 10 percent and preferably about 5 percent of the length of diaper 10. The waistband regions comprise those upper portions of diaper 10, which when worn, wholly or partially cover or encircle the waist or mid-lower torso of the wearer. In particular aspects of the invention, backsheet 30 provides front and/or rear waistbands 12, 14 which are substantially impermeable to liquid. In other aspects of the invention, backsheet 30 can provide front and/or rear waistbands 12, 14 which are substantially impermeable to both liquid and air.

The intermediate, crotch region 16 lies between and interconnects waistband regions 12 and 14, and comprises that portion of diaper 10 which, when worn, is positioned between the legs of the wearer and covers the lower torso of the wearer. Thus, the crotch region 16 is an area where repeated fluid surges typically occur in diaper 10 or other disposable absorbent article.

Topsheet 28 presents a body-facing surface which is compliant, soft-feeling, and non-irritating when contacting the wearer's skin. Further, topsheet 28 can be less hydrophilic than retention portion 48, and is sufficiently porous to be liquid permeable, permitting liquid to readily penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32.

Various woven and nonwoven fabrics can be used for topsheet 28. For example, the topsheet may be composed of a meltblown or spunbonded web of polyolefin fibers. The topsheet may also be a bonded-carded-web composed of natural and synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant.

In the illustrated embodiment, two containment flaps 62 are connected to the bodyside surface of topsheet layer 28. Suitable constructions and arrangements for containment flaps 62 are described, for example, in U.S. Pat. No. 4,704,116 issued Nov. 3, 1987, to K. Enloe, the disclosure of which is hereby incorporated by reference to the extent that it is consistent herewith.

Containment flaps 62, in the shown arrangements, are attached to topsheet layer 28 along fixed edges 64 of the flaps. A movable edge 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex Lycra elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. The containment flaps may be constructed of a material which is the same as or different than the material comprising topsheet 28. In optional embodiments, the containment flaps may be constructed of a material which is the same as or different than the material comprising surge management portion 46. The containment flaps may be composed of a material which is air permeable, liquid permeable, substantially liquid impermeable or combinations thereof.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 30 prevents the exudates contained in absorbent structure 32 from wetting articles such as bedsheets and overgarments which contact diaper 10. The backsheet may be a unitary layer of material or may be a composite layer composed of multiple components assembled side-by-side or laminated.

The shown embodiment of backsheet 30 includes protruding ear sections which extend laterally at the waistband portions 12 and 14 of the diaper. The ear sections cooperate with the crotch section of backsheet 30 to operably provide leg opening regions for positioning about the legs of the wearer.

In particular embodiments of the invention, backsheet 30 is a polyethylene film having a thickness of from about 0.012 millimeters to about 0.051 millimeters. In the shown embodiment, the backsheet is a film having a thickness of about 0.032 millimeters. Alternative constructions of the backsheet may comprise a woven or nonwoven fibrous web layer which has been totally or partially constructed or treated to impart the desired levels of liquid impermeability to selected regions that are adjacent or proximate the absorbent body.

In a particular aspect of the invention, a terminal edge of the substantially liquid impermeable backsheet material extends to a position which is substantially coterminous with a front or rear waistband edge of the backsheet member. In the illustrated embodiment, for example, a polymer film comprising backsheet 30 extends to a position which is substantially coterminous with a front or rear waistband edge of the backsheet.

Backsheet 30 typically provides the outer cover of the article. Optionally, the article backsheet may comprise one or more separate layers which are in addition to the outer cover layer and may be interposed between the outer cover layer and the absorbent structure.

Backsheet 30 may optionally be composed of a microporous, "breathable" material which permits water vapor to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minnesota. The backsheet can also be embossed or otherwise be provided with a matte finish to exhibit a more aesthetically pleasing appearance.

The size and shape of backsheet 30 is typically determined by the size of absorbent structure 32 and the exact diaper design selected. Diaper 10 may, for example, have a generally T-shape, a generally I-shape or a modified hourglass shape, and can define front and/or rear ear portions 38 and 40, respectively. The backsheet may extend beyond the terminal edges of absorbent structure 32 by a selected distance, such as a distance within the range of about 1.3 centimeters to 20.3 centimeters (about 0.5 to 8 inch).

Topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30. The above-described attachment means may also be employed to interconnect and assemble together the other component parts of the article.

Fastening means, such as tape tab fasteners 36, are typically applied at the lateral, side ends of the back waistband region 14 of diaper 10 to provide a mechanism for holding the diaper on the wearer in a conventional manner. Tape tab fasteners 36 can be any of those well known in the art, and are typically applied to the corners of diaper 10. Suitable adhesive tape fasteners are described in U.S. Pat. No. 5,147,347 issued Sep. 15, 1992 to Y. Huang et al. (Attorney Docket No. 9871), the disclosure of which is hereby incorporated by reference to the extent that it is consistent herewith.

Elastic members 34, 42 and 44 are disposed adjacent periphery 18 of diaper 10. Along each side edge region 20, leg elastic members 34 are arranged to draw and hold diaper 10 against the legs of the wearer. Waist elastic members, such as rear waist elastic 42, may also be disposed adjacent either or both of the end edges 22 of diaper 10 to provide elasticized waistbands.

The elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other means, such as heat-shrink elastic material, may be used to gather the garment.

In the embodiment illustrated in FIG. 1, leg elastic members 34 extend essentially along the complete length of crotch region 16 of diaper 10. Alternatively, elastic members 34 may extend the entire length of diaper 10, or any other length suitable providing the arrangement of elastically contractible lines desired for the particular diaper design.

Elastic members 34, 42 and 44 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hot melt adhesive. The various configurations of the invention may have the elastic members located on the inwardmost, bodyside surface of topsheet 28. Alternatively, the elastic members may be interposed between topsheet 28 and backsheet 30.

In the representatively shown embodiments of the invention, the illustrated leg elastic members 34 may comprise a carrier sheet 37 to which are attached a grouped set of elastics composed of a plurality of individual elastic strands 39. The elastic strands may intersect or be interconnected, or be entirely separated from each other. The shown carrier sheet may, for example, comprise a 0.002 cm thick film of unembossed polypropylene material. The shown elastic strands can, for example, be composed of Lycra ® elastomer available from DuPont, a business having offices in Wilmington, Delaware. Each elastic strand is typically within the range of about 620–1050 decitex (dtx), and can be about 940 dtx in an embodiment of the invention wherein three strands are employed for each elasticized legband.

Leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 1.9–3.8 centimeters (about 0.75–1.5 inches) inward from the outer most edge of the set of elastic strands. In particular arrangements, the curvature of the elastics may not be configured or positioned symmetrically relative to the lateral centerline of the diaper. As representatively shown in FIG. 1, the curved elastics may have an inwardly bowed and outwardly bowed, reflexed-type of curvature, and the length-wise center of the elastics may be offset by a selected distance within the range of about 0–8 cm toward either the front or rear waistband of the diaper to provide desired fit and appearance. In particular embodiments of the invention, the innermost point (apex) of the set of curved elastics can be offset about 0–12 cm towards the front or rear waistband of the diaper, and the outwardly bowed reflexed-portion can be positioned toward the diaper front waistband.

The shown embodiment of the invention includes a first waist elastic member 42 located at rear waistband portion 14 of diaper 10, and a second waist elastic member 44 positioned at front waistband portion 12. Optional configurations of the invention, however, may include only a single waist elastic member placed at either the front or rear waistband of the diaper. For example, the diaper may include only one waist elastic member located along the rear diaper waistband. Waist elastic 42 can be positioned in the rear end margin 22 provided by backsheet 30, and can be located in a substantially co-linear, cross-directional alignment with the shown pair of fastener tabs 36.

The waist elastic members can have a laterally extending, cross-directional width dimension which is within the range of about 20–80 percent of article width 92. Alternatively, the waist elastic width dimension is within the range of about 25–60 percent of article width 92, and optionally, is within the range of about 40–50 percent of the article width. In particular aspects of the invention, waist elastics 42 and/or 44 can have a cross-directional width dimension within the range of about 5–33 centimeters. Alternatively, the cross-dimensional width dimension of the waist elastic is within the range of about 10–20 centimeters, and optionally is within the range of about 12–16 centimeters.

A waist elastic member 42 or 44 can also have a longitudinally extending length dimension which is within the range of about 1–10 centimeters. Alternatively, the length dimension of the waist elastic is within the range of about 2–8 centimeters, and optionally, is within the range of about 2.5–5 centimeters.

The elastic members, such as waist elastics 42 and 44, can be composed of an elastomeric, cloth-like nonwoven fibrous material, such as an elastomeric stretch-bonded laminate (SBL) web or an elastomeric meltblown web. Examples of suitable meltblown elastomeric fibrous webs for forming the elastic members are described in U.S. Pat. No. No. 4,663,220 issued May 5, 1987, to T. Wisneski, et al., the disclosure of which is hereby incorporated by reference to the extent that it is consistent with the present description. Examples of composite fabrics comprising at least one layer of nonwoven textile fabric secured to a fibrous elastic layer are described in European Patent Application EPA 0 110 010 published Apr. 8, 1987, with the inventors listed as J. Taylor et al., the disclosure of which is hereby incorporated by reference to the extent that it is consistent herewith. The composite nonwoven fabrics are commonly referred to as stretch-bonded laminates.

In yet another aspect of the invention, the elastic members, such as waist elastics 42 and 44, can be composed of an elastomeric, stretchable composite web comprising individual, discrete strips of elastomeric material secured to one or more nonwoven fibrous layers. Such a composite web may, for example, comprise an elastomeric meltblown material arranged in a selected pattern of strips and suitably sandwiched and attached between two layers of nonwoven, spunbonded fibrous material. The composite web may alternatively comprise a selected pattern of individual elastomeric strips operably secured to a nonwoven fibrous layer or between two nonwoven layers. The elastomer strips may, for example, be composed of a thermoplastic, melt extrudable material. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

An absorbent body, such as absorbent structure 32, is positioned between topsheet 28 and backsheet 30 to form diaper 10. The absorbent body has a construction which is generally compressible, conformable, non-irritating to the wearer's skin. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Alternatively, each piece is connected to an adjacent portion of the absorbent structure by a suitable bonding and/or fiber entanglement mechanism, such as ultrasonic or adhesive bonding, or mechanical or hydraulic needling.

Absorbent structure 32 includes a retention portion 48 which is capable of absorbing and retaining liquid body exudates. In the embodiment illustrated by FIG. 5, for example, retention portion 48 can include an absorbent laminate 112 which is supplemented with a distribution layer 120.

Absorbent structure 32 includes a back section 51 and a front section 49, and provides a liquid acquisition, target zone 53. The absorbent structure has a contoured, curvilinear periphery, particularly along its side edges. The two generally mirror-image, inwardly bowed, lateral edges provide for a narrower intermediate section suitable for positioning in the crotch of the wearer.

In the representatively shown embodiment of absorbent structure 32, front section 49 can be conceptually divided into three regions comprising two transversely spaced ear regions 50 and 52 respectively, and a central region 54.

Ear regions 50 and 52 comprise portions which generally extend from the lateral side edges of the absorbent structure toward longitudinal center line 58 a distance from one-tenth to one-third of the overall width of absorbent structure 32, and connect to central region 54. When the diaper is worn, the ear regions are configured to generally engage the sides of the wearer's waist and torso, and central region 54 is configured to generally engage the medial portion of the wearer's waist and torso.

With respect to absorbent articles, wherein reduced bulk or reduced cost may be important, the surge management and retention portions need not extend over the entire, overall shape of the garment. In the shown aspects of the invention, for example, absorbent structure 32 can include a retention portion 48 which has a length 94 which is not more than about 90 percent of article length 90. Alternatively, the retention portion has a length 94 which is not more than about 80 percent of article length 90, and optionally, has a length which is not more than about 70 percent of the article length to better provide desired benefits. In particular aspects of the invention, the retention portion has a length 94 which is not less than about 40 percent of article length 90. Alternatively, the retention portion has a length 94 which is not less than about 50 percent of article length 90, and optionally has a length which is not less than about 60 percent of the article length to better provide desired performance.

In particular aspects of the invention, retention portion 48 can be asymmetrically located along the length of backsheet 30, with at least about 45 percent of the retention portion length 94 located in a front half-section of backsheet 30. Alternatively, at least about 55 percent of the retention portion length is located in the front half-section of backsheet 30, and optionally, at least about 65 percent of the retention portion length is located in the front half-section of the backsheet to provide desired attributes.

In other aspects of the invention, a selected region of the retention portion, such as distribution layer 120, can include a liquid-permeable wrap sheet layer 70 having a length 69 which is not more than about 50 percent larger than the length of retention portion 48. Alternatively, wrap sheet length 69 is not more than about 25 percent larger than the length of retention portion 48, and optionally, is not more than about 10 percent larger than the length of the retention portion to provide desired benefits.

Retention portion 48 can be asymmetrically located along the length of wrapsheet 70, with at least about 55 percent of the weight of the retention portion located in a front half-section of wrapsheet 70. Alternatively, at least about 65 weight percent (wt %) of the retention portion is located in the front half-section of wrapsheet 70, and optionally, at least about 75 wt % of the retention portion length is located in the front half-section of the wrapsheet.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

In a particular aspect of the invention, the absorbent structure has an absorbent capacity of at least about 100 gm of saline. Optionally, the absorbent capacity can be at least about 200 gm of saline. Alternatively, the absorbent structure has an absorbent capacity of at least about 300 gm of saline, and optionally has an absorbent capacity of at least about 400 gm of saline to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a Cahn SFA-222 Surface Force Analyzer System. When measured with this system, fibers having contact angles less than 90° are designated "wettable", while fibers having contact angles greater than 90° are designated "nonwettable".

Figure 6:
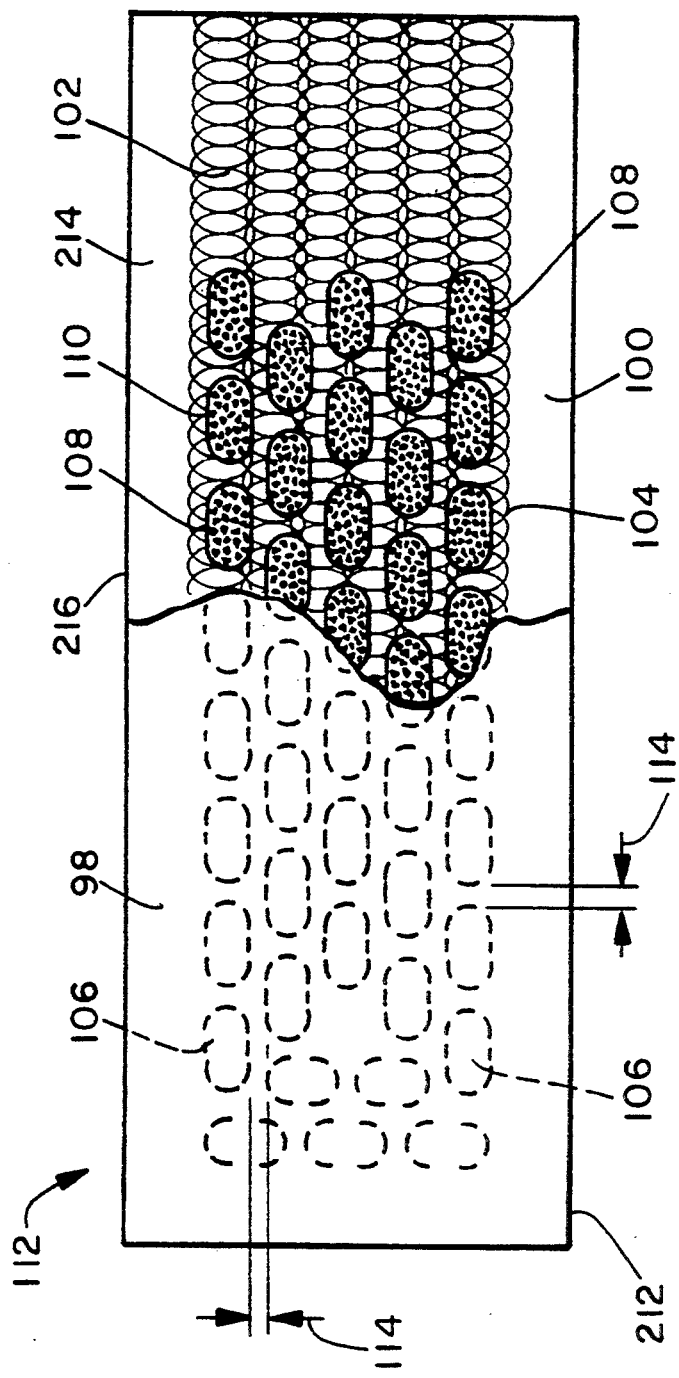
FIG. 6 representatively shows a partially cut-away, top view of an absorbent laminate of the invention.
Figure 7:
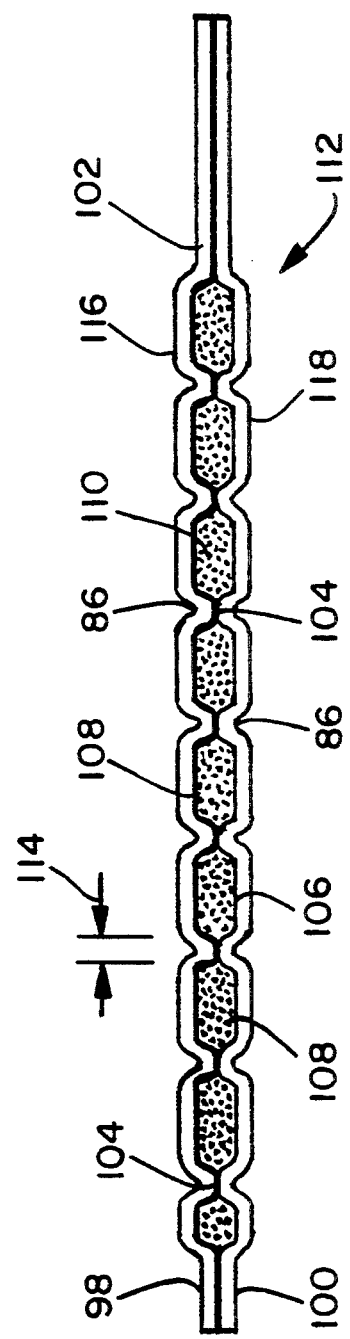
FIG. 7 representatively shows a cross-sectional, side view of the absorbent laminate illustrated in FIG. 6.

As representatively shown in FIGS. 5–7, at least a portion of retention portion 48 is situated in target zone 53, and can be configured to substantially define the boundaries of absorbent structure 32. More particularly, the retention portion can comprise a first, liquid permeable carrier layer 98 and at least a second carrier layer 100. A water sensitive attaching means, such as a mechanism comprising water-sensitive adhesive 102, secures together carrier layers 98 and 100 to provide substantially attached zones 104 and a multiplicity of substantially unattached zones 106 thereof. The substantially unattached zones 106 provide a plurality of pocket regions 108, and a high absorbency material, such as particles of superabsorbent material 110, is located within pocket regions 108 to provide an absorbent laminate 112.

Various techniques may be employed to construct absorbent laminate 112. For example, selected quantities of particulate superabsorbent material may be segregated at predetermined pocket locations of carrier layer 100 and adhesive 102 may be sprayed or otherwise applied to carrier layer 98 in a generalized pattern or specific localized patterns, using conventional techniques. Carrier layer 98 can then be laminated onto carrier layer 100 to sandwich the segregated quantities of superabsorbent particles therebetween. The two carrier layers can adhere to each other at the interstitial regions between the individual pockets and at the marginal regions around the outer periphery of the pattern of pocket locations. The pattern of pocket locations will define the desired pocket array, and the overall assembly can provide an operable absorbent laminate 112.

Carrier layer 98 may be composed of a wettable or nonwettable material, and in the shown embodiment is composed of a wettable fibrous web. Suitable fibrous webs may be provided by hydraulically needled nonwoven pulp fiber webs, webs composed of cellulosic tissue, webs composed of meltblown fibers or the like.

A fibrous web comprising carrier layer 98 can have a basis weight within the range of about 5–400 gsm (grams per square meter), and desirably can have a basis weight within the range of about 5–100 gsm. Alternatively, the basis weight can be within the range of about 10–50 gsm, and optionally, can be within the range of about 10–30 gsm to provide desired benefits. Where carrier layer 98 comprises a fibrous synthetic polymer web, such as a meltblown web, the fibers may be composed of polyethylene, polypropylene, polyester, rayon, Hydrofil ®, or the like.

Second carrier layer 100 may be composed of a material which is the same as or different than the material comprising first carrier layer 98. Second carrier layer 100 may be liquid permeable or substantially liquid impermeable, and in the shown embodiment is liquid permeable. In addition, second carrier layer 100 in the illustrated embodiment is composed of a wettable fibrous web, but may be composed of a nonwettable fibrous web.

In the various arrangements of the invention, the carrier layers may be colored or otherwise visually highlighted to provide aesthetic benefits. For example, the sections of carrier layer material at the pocket regions of the absorbent laminate may be colored to provide visual cues regarding the presence or performance of the distinctive aspects of the absorbent structure.

In the illustrated embodiment, first carrier layer 98 is positioned toward the bodyside of absorbent laminate 112, and is composed of a wettable, liquid permeable, cellulosic tissue having a selected level of wet strength and a basis weight of about 22 gsm. Similarly, second carrier layer 100, which is positioned toward the outer side of absorbent laminate 112, is composed of a wettable, liquid permeable, cellulosic tissue having a selected level of wet strength and a basis weight of about 17 gsm.

The water-sensitive attaching means for securing together carrier layers 98 and 100 along attached zones 104 may comprise mechanical bonding, such as stitching, needling or the like, as well as water-sensitive thermal bonding, hydrogen bonding, adhesive bonding or the like. In the illustrated embodiment, for example, the water-sensitive carrier attachment means includes a selected pattern of water-sensitive adhesive 102. Various types of water-sensitive adhesive can be configured for use in the present invention. Suitable adhesives can include, for example, National Starch 70-3998 CYCLO-FLEX (a hot melt adhesive which is composed of a graft copolymer comprising a vinyl monomer, a polyalkylene oxide polymer and a proportion of polyethylene oxide ), National Starch 33-2058 (a polyvinylacetate-based latex), and the like. National Starch adhesives are available from National Starch and Chemical Co., a business having offices in Bridgewater, New Jersey.

For the purposes of the present description, the term, water-sensitive attaching (or attachment) means refers to an attachment system wherein the strength of the attachment system is great enough to adequately hold the carrier layers 98 and 100 together when the system is substantially dry and when the system is wet. In addition, the wet-strength of the attachment system is configured to be sufficiently low so as to not excessively constrict the swelling expansion of the high absorbency material during the absorption of liquid. The wet-strength of the attachment system is less than the separating force imparted by the swelling of the high absorbency material when the high absorbency material is exposed to aqueous liquids, such as urine. In addition, the water-sensitive attachment system is configured to release at an applied load which is less than the load needed to delaminate the water-sensitive attaching means without excessively tearing the material forming either or both of the carrier layers when such layers are wetted. The water-sensitive attachment system is also configured to release at an applied load which is less than the load needed to excessively burst the material forming either or both of the carrier layers when such layers are wetted. Typically, the applied load is a generally tensile load resulting from the pressure exerted by the expanding high absorbency material when the material absorbs liquid and swells. The appropriate attachment system components, such as carrier sheets 98 and 100, are constructed and arranged to be sufficiently strong to withstand this pressure and substantially avoid bursting or tearing.

In other aspects of the invention, the securing strength of the attachment system is greater than zero, and desirably is at least about 0.05N/cm when the attachment system is wetted. In a particular aspect of the invention, the strength of the attachment system can be arranged to change in response to the presence of the aqueous liquids. More particularly, the attachment strength of the attachment system when it is contacted with an aqueous liquid can be configured to be less than the attachment strength of the substantially dry attachment system. The relative decrease in attachment strength may, for example, arise from a degradation in the mechanism of interconnection between the carrier layers. For example, where the attaching means comprises an adhesive bond, the bonding strength of the adhesive may be configured to decrease upon a selected exposure to moisture, thereby providing a desired degree of water-sensitivity. Alternatively, the water-sensitivity of the attaching means may arise from a degradation in the strength of the material forming either or both carrier layers. For example, where a carrier layer is composed of a wet-strength cellulosic tissue, the strength of the tissue when wetted may be configured to decrease to a level which permits an operable release from its securement to the other carrier layer. Where a carrier layer includes meltblown fibers, the meltblown layer may be constructed to have a wet-strength which decreases to a level which permits an operable release from its securement to the other carrier layer. The decreased wet-strength of a meltblown web may, for example, be provided by tailoring the composition of the web material and tailoring the interfiber structure of the web. Optionally, the water-sensitivity of the attaching means may arise from a combination of a degradation in the mechanism of interconnection between the carrier layers and a degradation in the strength of the material forming either or both carrier layers.

In the various configurations of the invention, the bonded attached zones 104 of the absorbent laminate 112 are constructed with sufficient integrity to isolate and contain the high absorbency material within each pocket. The securement strength between carrier layers 98 and 100 is at least about 0.05N/cm, peak force, when the absorbent laminate is substantially dry. Alternatively the dry securement strength is at least about 0.08N/cm, and optionally is at least about 0.1N/cm to provide desired benefits.

When absorbent laminate 112 is wet, the securement strength between carrier layers 98 and 100 along attached zones 104 is constructed to be sufficient to maintain the general integrity of the absorbent laminate. In particular aspects of the invention, the wet securement strength is not less than about 0.04N/cm peak force. Alternatively, the wet securement strength is not less than about 0.07N/cm, and optionally is not less than about 0.09N/cm to provide desired benefits.

In desired configurations of the invention, the wet securement strength between carrier layers 98 and 100 is configured so as to not excessively limit the swelling and expansion of the high absorbency material when the material is absorbing liquids, such as urine. Particular aspects of the invention can be configured so that the wet securement strength between carrier layers 98 and 100 not more than about 5N/cm, peak force. Alternatively, the wet securement strength is not more than about 2N/cm, and optionally, is not more than about 1N/cm to provide desired performance.

For the purposes of the present invention, a suitable technique for determining the dry or wet securement strength of the attaching means is the ASTM Standard Test Method for Peel Resistance of Adhesives ("T-Peel Test); Designation: D 1876-93, approved Jan. 15, 1993; which is described in detail in the EXAMPLES section hereinbelow.

In further aspects of the invention, the saturated, expansion and swelling of the high absorbency material within the absorbent laminate 112 is at least about 90% of the saturated, free-swell volume of the high absorbency material. Alternatively, the saturated expansion of the high absorbency material within the absorbent laminate is at least about 95%, and optionally is at least about 97% of the saturated, free-swell volume of the high absorbency material to provide improved performance.

A suitable technique for determining the saturated, free-swell volume of the high absorbency material within the absorbent laminate is the Free-Swell procedure described in detail in the EXAMPLES section hereinbelow.

A suitable technique for determining the saturated, expansion swelling of the high absorbency material within the absorbent laminate is the Laminate-Swell procedure described in detail in the EXAMPLES section hereinbelow.

In the various aspects of the invention, carrier layers 98 and 100 can be configured with sufficient wet-strength to withstand the pressure generated by the expanding high-absorbency material 110 prior to the substantial release of the wet securement between the carrier layers. As a result, the wet carrier layers can maintain sufficient integrity substantially without tearing as the high-absorbency material absorbs liquid and swells. Particular aspects of the invention can include carrier layers either or both of which are composed of a material having a peak, wet burst strength of at least about 0.08N/cm. Alternatively, the carrier layer material can have a burst strength of at least about 0.10N/cm, and optionally can have a burst strength of at least about 0.12N/cm to provide improved performance.

For the purposes of the present invention, a suitable technique for determining the burst strength of the carrier layer material is the following procedure:

WET BURST TEST PROCEDURE

Materials and Equipment
a) Compression test instrument (or tensile test instrument adapted to operate in a compression mode) such as available from Instron or Sintech equipped with a load cell capable of measuring in the 0.01N to 5N range. The test instrument is configured to record the peak force applied to the probe as it penetrates the carrier sheet.
b) Solid cylindrical probe, 1.27 cm diameter, at least 10 cm long. The end which strikes the carrier sheet is convex hemispherical. The probe is mounted on the compression test instrument such that the probe descends vertically at 48 cm/min when activated.
Hollow cylindrical sample holder, 6.35 cm internal diameter, approximately 8 cm outer diameter. The sample holder is to be smooth and rounded on the inside, upper end so as not to prematurely tear the sample.
d) Ring clamp to hold the sample to the top of the sample holder. One suitable method of holding the ring clamp securely to the sample holder is to use magnets.
e) Test solution, either distilled water or 0.85% saline (blood bank saline, nominally 8.5 gm of sodium chloride per liter of water, such as available from Baxter Healthcare Corporation, McGaw Park, Illinois or from Stephens Scientific Division of Cornwell Corporation, Riverdale, New Jersey), as appropriate.
Procedure
a) Samples are cut into 12.7×12.7 cm squares. Materials are conditioned for at least 48 hours, and testing is conducted at ambient conditions of 23±1° C. and a relative humidity of 50±2%.
b) Center the sample over the sample holder, and clamp it into place.
c) Center the sample holder under the probe.
d) Add approximately 0.25 ml of test solution.
e) Wait 30 seconds, then actuate the probe so that the probe penetrates the sample.
Calculation
Peak force is read from the instrument display or recorder. Units are converted to Newtons, if necessary. To present as N/cm, divide the peak force by the circumference of the probe (3.99 cm).

The wet burst strength of several potential carrier sheets was determined using the procedure described above. Each mean and standard deviation in the following table is based on 20 samples.

For the Peak Load per unit length (N/cm): the diameter of the circular probe used in this procedure was 1.27 cm; and these data represent the load divided by the probe circumference.

| Material | Test Solution | Peak Load Burst (Newtons) | | Burst Strength (N/cm) | |
|---|---|---|---|---|---|
| | | mean | std | mean | std |
| Barrier Tissue | water | 0.67 | 0.11 | 0.168 | 0.028 |
| Forming Tissue | water | 0.82 | 0.11 | 0.206 | 0.028 |
| Kleenex ® Facial Tissue | water | 0.30 | 0.04 | 0.075 | 0.010 |
| Puffs ® Facial Tissue | water | 0.24 | 0.05 | 0.060 | 0.013 |
| Hi-Dri ® Towel | water | 0.86 | 0.09 | 0.216 | 0.023 |
| Bounty ® Towel | water | 1.46 | 0.15 | 0.366 | 0.038 |
| Barrier Tissue | saline | 0.54 | 0.07 | 0.135 | 0.018 |
| Forming Tissue | saline | 0.64 | 0.08 | 0.160 | 0.020 |
| Barrier Tissue | water | 0.49 | 0.12 | 0.123 | 0.030 |

"std" = standard deviation
"barrier tissue" = 21 gsm cellulose tissue
"forming tissue" = 17 gsm cellulose tissue These materials are known to show batch-to-batch variability as well as variability within a batch, hence the data above suggest ranges of burst strength for some potential carrier materials. Some potential carrier materials, such as some spunbonded nonwovens, for example, may far exceed the strengths of the tissues and paper towels reported above.

In the various configurations of the invention, the water-sensitive attaching means and the strengths of the carrier layers 98 and 100 can be selectively configured to permit the expansion of the wetted high absorbency material in an arrangement that substantially avoids a bursting of at least one of the carrier layers. A bursting of a carrier layer is a visible tear which occurs in a carrier layer and is at least 3 mm in length. Particular aspects of the invention can be advantageously configured to provide an absorbent laminate 112 wherein not more than about 25% of the pocket regions, which contain high-absorbency material, burst when exposed to an excess of saline solution. To provide improved performance, the absorbent laminate can alternatively have a configuration wherein not more than about 15% of such pocket regions burst, and can optionally have a configuration wherein not more than about 10% of such pockets burst when exposed to the excess of saline solution.

A suitable technique for determining the propensity of the absorbent laminate 112 to burst is to place the absorbent composite in a transparent tray containing an amount of 0.85% saline which exceeds the amount needed to saturate absorbent laminate. After the laminate has remained in the tray of saline for 15 minutes, the top and bottom carrier layers of the laminate are inspected for the presence of visible tears which are at least 3 mm in length. The number of pockets with any such tears divided by number pockets containing high absorbency material (times 100) yields the percentage of burst pockets.

Where the water-sensitive attaching means comprises an adhesive system which exhibits decreased attachment strength when wet, the selective, wet-releasability of adhesive 102 can advantageously allow the size of pockets 108 to expand as the high absorbency material swells. As a result, the high absorbency material is better contained in position and reduces the likelihood of rupturing carrier layers 98 and 100 when the high absorbency material swells.

Adhesive 102 can be applied onto either or both of carrier sheets 98 and 100. In the illustrated embodiment, for example, adhesive 102 is applied onto only one of carrier sheets 98 and 100, such as carrier sheet 100. In such structures, only one side of the quantity of high absorbency material contained in each pocket 108 will be in contact with a carrier layer having adhesive applied thereon.

In one aspect of the invention, adhesive 102 is applied in a selected pattern, such as a sprayed pattern of discrete globules, a swirled pattern of adhesive filaments, a regular or irregular network of adhesive filaments, a pattern of printed adhesive, a generally random application of printed adhesive, or the like. Adhesive 102 can be provided at an add-on amount of adhesive solids which is at least about 1 gram per square meter of adhered area. Alternatively, the adhesive is provided at an add-on amount of at least about 7.5 grams per square meter, and optionally is provided at an add-on amount of at least about 10 grams per square meter. In other aspects of the invention, the adhesive add-on amount is not more than about 150 grams per square meter of adhered area. Alternatively, the adhesive add-on amount is not more than about 65 grams per square meter, and optionally is not more than about 40 grams per square meter.

In the various embodiments of the invention, adhesive 102 can be provided in an arrangement which retains high absorbency material 110 within a selectively configured distribution which substantially fills the volume of each pocket 108. Such a configuration can better maintain the placement and distribution of high absorbency material within each pocket. By avoiding excessive unfilled free volume within each pocket 108, the high absorbency material can be substantially prevented from excessively bunching up or accumulating in an isolated section of each pocket. As a result, the absorbent capacity of the high absorbent material can be more efficiently utilized.

The substantial filling of pocket regions 108 can be determined with respect to an article laid out with the plane of the absorbent laminate in a substantially horizontal position. In this position, the projected area of the individual pockets 108 is substantially completely covered by the projected area of the high absorbency material contained in each pocket. In particular configurations, the projected area of the high absorbency material (projected substantially perpendicular to the general plane of the absorbent laminate) covers at least about 60% of the projected area of each pocket. Alternatively, the projected area of the high absorbency material covers at least about 75% of the projected area of each pocket, and optionally the projected area of the high absorbency material covers at least about 95% of the projected area of each pocket to provide desired performance. In other configurations, the projected area of the high absorbency material covers about 100% of the projected area of each pocket to provide desired benefits.

Within the individual pocket regions, the particles of high-absorbency material readily contact one another and are not kept substantially separated apart by some other material. As a result, the absorbent laminate 112 can have enhanced thinness and can avoid the excessive bulkiness caused by the presence of other materials. At least about 90 wt % of the material contained within the pocket regions is composed of the high-absorbency material. Alternatively, at least about 95 wt %, and optionally, at least about 97 wt % of the contained material is composed of the high-absorbency material.

In a particular aspect of the invention, attached zones 104 are configured as a regular or irregular series of non-intersecting rings positioned around each of pocket regions 108. The attached zone rings may be regular or irregular in configuration and may be circular or non-circular in shape, as desired.

Within attached zones 104 of the absorbent laminate, the attaching means holds together the carrier layers 98 and 100 to operably define channel regions 86 located and extending between immediately adjacent individual pockets. The channels can help to more effectively and more rapidly distribute liquids to the high absorbency material held in each of the pocket regions. The water-sensitivity of the attaching means is selected to operably regulate and control the release of the attachment and thereby more efficiently maintain the presence and operability of the channel regions during the absorption process. As a result, when some regions of absorbent laminate are relatively more wetted than other regions, the operability of channels 86 can continue to provide substantially unrestricted flow paths through the more wetted regions to the less wetted regions of the absorbent laminate.

The non-wetted areas of the absorbent laminate can maintain the controlled positioning of the high-absorbency material while the wetted areas of the laminate can release in localized regions to permit an expansion of the high-absorbency material. The expansion of the wetted high-absorbency material does not interfere with the selected positioning and distribution of the high-absorbency material in the non-wetted areas of the laminate.

For example, in typical absorbent articles, liquids primarily enter absorbent laminate 112 at the target section of the absorbent structure, and the pocket regions in the target section can become wetted and even saturated prior to wetting and saturating the pocket regions in sections of the absorbent structure that are relatively more remote from the target section. With the distinctive, controlled preservation of channels 86, however, liquids can readily flow around and past the more wetted and swollen pockets of high absorbency material to reach the more remote, less wetted pockets of high absorbency material. As a result, the complete absorbent capacity of substantially the entire absorbent structure, particularly the entirety of absorbent laminate 112, can be more efficiently utilized. The invention can advantageously provide a structure wherein the swelling of the pocket regions in the target section of the article does not excessively inhibit the flow of liquid to the pocket regions outside of the target section.

In one aspect of the invention, liquid permeable carrier layer 98 is configured to efficiently wick aqueous liquids. For example, to provide desired levels of wickability, carrier layer 98 is capable of transporting at least 0.3 grams of saline per minute per gram of carrier layer material measured at a wicking height of 10 centimeters. Alternatively, carrier layer 98 exhibits a liquid transporting value of at least about 0.6 grams of saline per minute per gram of carrier layer material, and optionally exhibits a liquid transporting value of at least about 2 grams of saline per minute per gram of carrier layer material.

In another aspect of the invention, carrier layer 98 can include a pattern of embossments formed thereon with the embossed areas having a relatively higher density than the unembossed areas thereof. In the shown embodiments of the invention, the forming of the embossments or the presence of the embossments does not provide securement between carrier layers 98 and 100 along attached zones 104.

At least 80 percent of the high absorbency material contained within absorbent laminate 112 is held within pocket regions 108. In particular arrangements, at least about 90 percent of the high absorbency material within the absorbent laminate structure is contained within the pocket regions. Alternatively, at least about 95 percent of the high absorbency material within the absorbent laminate is contained within the pocket regions, and optionally, about 100 percent of the high absorbency material is held within the pocket regions to provide desired levels of performance. Accordingly, not more than about 20 percent of the high absorbency material is held within attached zones 104 of the absorbent laminate. Alternatively, not more than about 10 percent of the high absorbency material is held within attached zones 104, and optionally, not more than about 5 percent of the high absorbency material is contained within the attached zones to provide desired benefits.

The total amount of high absorbency material contained within absorbent laminate 112 may be non-uniformly or substantially uniformly distributed among the plurality of pockets 108. Substantially equal amounts of high absorbency material may be contained within each individual pocket 108. Alternatively, different amounts of high absorbency material may be contained in selected pocket regions. Particular aspects of the invention are configured with none of the individual pockets containing more than 200 percent of the mean mass of high absorbency material contained in each of the pocket regions. In particular arrangements of the invention, the mean mass of high absorbency material in each pocket region is at least about 0.05 gram. Alternatively, the mean mass of high absorbency material in each pocket region is at least about 0.1 grams, and optionally is at least about 0.15 grams to provide desired performance. In further aspects of the invention, the mean mass of high absorbency material in each pocket region is not more than about 2.0 grams. Alternatively, the mean mass of high absorbency material is not more than about 0.85 grams, and optionally is not more than about 0.30 grams to provide desired benefits. In the various embodiments of the invention, each pocket region can be approximately 100% filled with high absorbency material.

In unattached zones 106, there is substantially no direct bonding or interconnection between carrier layers 98 and 100. As a result, the unattached zones can provide individual pocket regions 108 of selected size. For example, each of the pocket regions can be configured to extend substantially continuously over an area of not less than about 0.25 cm$^2$. Alternatively, the pocket region size is not less than about 0.75 cm$^2$, and optionally, is not less than about 1.25 cm$^2$ to provide pocket regions 108 having desired characteristics. In further aspects of the invention, the individual pocket region size is not more than about 310 cm$^2$. Alternatively, the pocket region size is not more than about 70 cm$^2$, and optionally, extends over an area of not more than about 5 cm$^2$ to provide desired performance.

In addition, the overall system of pockets 108 can be positioned and arranged in desired patterns to provide a selected, operable pocket array 144 composed of the cooperating individual pockets. The pocket array, in one aspect of the invention, can provide a pattern size having an encompassed area extent of not less than about 5 cm². Alternatively, the pattern size is not less than about 20 cm², and optionally is not less than about 145 cm² to provide a pocket array having desired characteristics. In another aspect of the invention, the pocket array can provide a pattern size which, for adult care type garments is not more than about 4000 cm², and alternatively is not more than about 1000 cm². For an infant care article, the pattern size is not more than about 470 cm². Alternatively, the pocket region size is not more than about 390 cm², and optionally extends over an area of not more than about 310 cm² to provide desired performance.

In particular aspects of the invention, there is a discrete separation distance 114 between individual pockets 108, as representatively shown in FIGS. 6 and 7. Pocket spacing distance 114 is at least about 0.15 cm. Alternatively, the pocket spacing distance is at least about 0.25 centimeters, and optionally is at least about 0.3 centimeters to provide desired performance. In other aspects of the invention, pocket spacing distance 114 is not more than about 3 centimeters. Alternatively, the pocket spacing distance is not more than about 1.9 centimeters, and optionally is not more than about 1.2 centimeters, to provide desired performance. If the separation distance between individual pockets is too small, aqueous liquids may not be able to move along and across the surfaces of absorbent laminate 112 at a sufficiently rapid rate.

The absorbent laminate has a front waistband section 212, which is appointed for general positioning toward the front waistband section of the intended article, and a rear waistband section 214, which is appointed for general positioning toward the rear waistband section of the intended article. A crotch section 216 of the absorbent laminate is appointed for positioning at or about the intended crotch section of the article.

Figure 12:
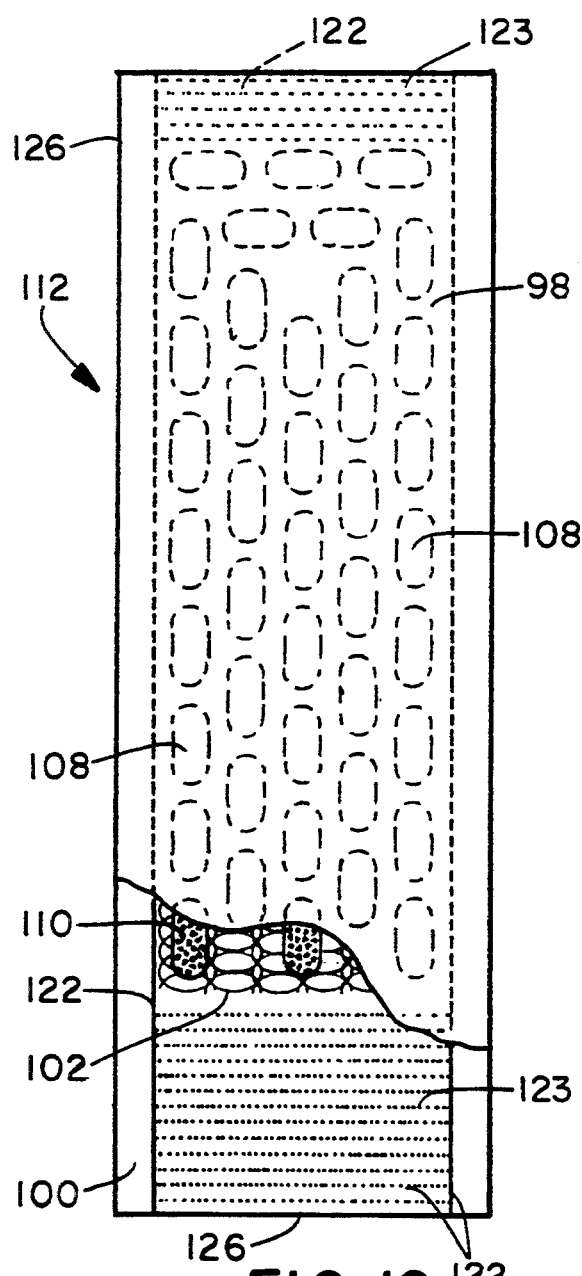
FIG. 12 representatively shows a partially cut-away, top plan view of an absorbent laminate having substantially water-insensitive, secondary attachments which extend along an entire periphery of the laminate.

With reference to FIG. 12, absorbent laminate 112 can include secondary attaching means 122 for securing together carrier layers 98 and 100 along selected secondary attachment regions 123 to provide a substantially water-insensitive attachment therebetween. Such secondary attachment means can, for example, be provided by adhesive surface bonds, adhesive encapsulation, mechanical fasteners, thermal bonds, sonic bonds, encapsulation mechanisms or the like. In an example of an encapsulation mechanism, one carrier layer can be overwrapped and appropriately fastened around the second carrier layer. The secondary attachment regions are substantially restricted to locations spaced from pocket regions 108 by a discrete distance.

Figure 13:
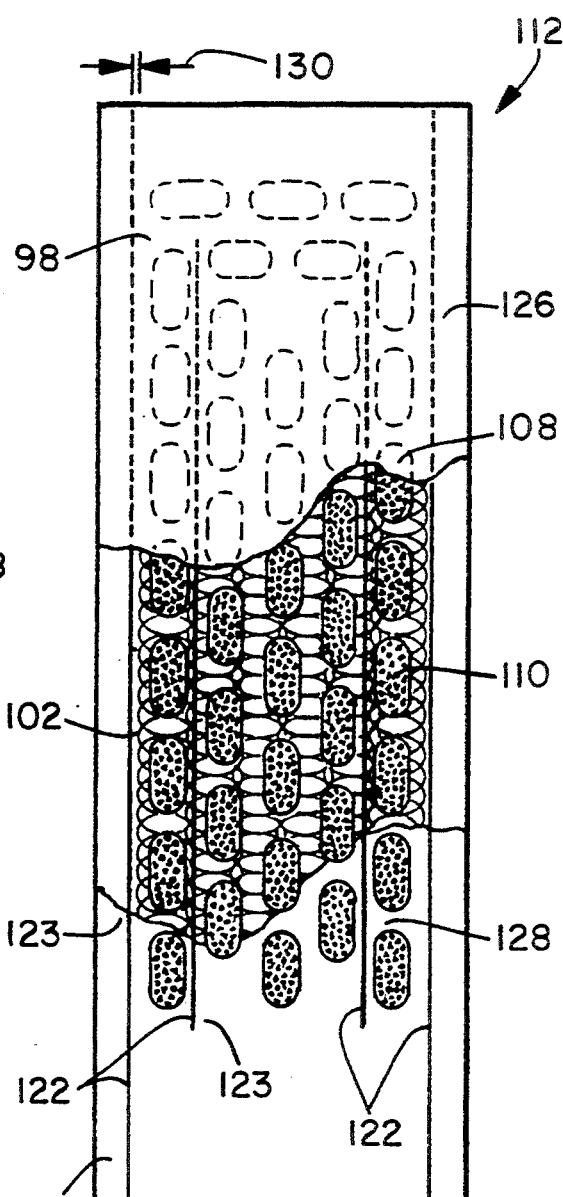
FIG. 13 representatively shows a partially cut-away, top plan view of an absorbent laminate having substantially water-insensitive, secondary attachments which extend along the lateral, side peripheries of the laminate, and representatively shows substantially water-insensitive, secondary attachment means located at interstitial locations between immediately adjacent pocket regions.

In one aspect of the invention, secondary attaching means 122 is substantially restricted to an outer periphery 126 of absorbent laminate 112. The secondary attachments may be configured to extend along both the longitudinally extending side peripheries and laterally extending end peripheries of the laminate, as representatively shown in FIG. 12. The secondary attachments may also be arranged to extend along only the longitudinally extending side peripheries of the laminate, as illustrated in FIG. 13.

In another aspect of the invention, secondary attachments 122 can also be positioned at interstitial locations 128 between immediately adjacent pocket regions 108. Additionally, as representatively shown in FIG. 13, the secondary attachments can extend along selected peripheral regions and selected interstitial regions.

Figure 14:
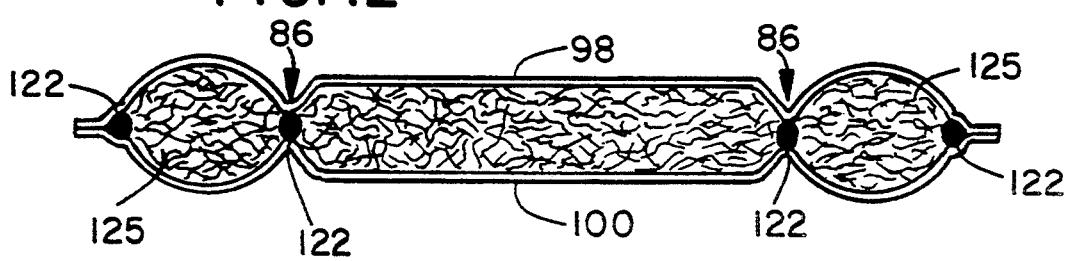
FIG. 14 representatively shows a cross-sectional view of a wetted absorbent laminate wherein substantially water-insensitive secondary attachment means have helped to maintain channel regions in the wetted laminate.

Secondary attachments 122 can be distinctively constructed and arranged to selectively block the releasing operation provided by water-sensitive attachments 102. The expansion and lateral growth of each individual absorbent pocket region 108 or selected groups of pockets can thereby be limited to a selected zone 125, as representatively shown in FIG. 14. As a result, the lateral expansion of one pocket is substantially prevented from interfering with the expansion of an adjacent pocket, the overall absorbent efficiency of the absorbent laminate can be enhanced. At the outer periphery 126 of absorbent laminate 112, secondary attachments 122 can advantageously block the undesired escape of swollen, absorbent gel material from the laminate structure. At interstitial locations 128, secondary attachments 122 can maintain channels 86 and thereby enhance liquid flow to less wetted regions of the laminate 112.

For the purposes of the present invention, the term water-insensitive attaching means (or water-insensitive attachment) refers to an attaching means which, when wet, has a relatively stronger securing strength than the respective wet strength of the water-sensitive attaching means. The relatively stronger securement strength can, for example, be provided for by a different, relatively stronger attaching mechanism, a relatively stronger adhesive, an adhesive provided at a relatively greater amount of add-on, an attachment provided by a relatively stronger bonding pattern, or the like.

Secondary attachments 122 can be arranged in selected configurations, such as lines, beads, swirls, spots or the like. The illustrated embodiments, for example, can include secondary attachments which comprise lines of substantially water-insensitive attachment, and in particular aspects of the invention, the attachment lines can be configured with a width dimension 130 of not more than about 3 cm. Alternatively, the attachment width dimension is not more than about 1 cm, and optionally, is not more than about 0.3 cm to provide desired attributes.

In addition, the secondary attachments at interstitial locations 128 can advantageously be spaced from each of the immediately adjacent pockets by a distance of not less than about 0.1 cm. Alternatively, the spacing is not less than about 0.5 cm, and optionally is not less than about 1 cm to provide desired performance. Further aspects of the invention can be configured with the secondary attachments at interstitial locations 128 selectively spaced from each of the immediately adjacent pockets by a distance of not more than about 5 cm. Alternatively, the spacing is not more than about 3 cm, and optionally is not more than about 2 cm to provide desired benefits.

In particular aspects of the invention, the wet strength of the secondary attachments can advantageously be at least about 0.09N/cm. Alternatively, the wet strength of the secondary attachments can be at least about 0.15N/cm, and optionally can be at least about 1N/cm to provide improved performance. In other aspects of the invention, the wet strength of the secondary attachments is at least about 5 N/cm, and alternatively is at least about 10N/cm to provide desired characteristics.

In the various configurations of the invention, the secondary attachment means can be constructed to provide a Peripheral (Perimeter) Release value which is not more than 15%. Alternatively, the Peripheral Release value is not more than about 10%, and optionally, is not more than about 5% to provide desired characteristics. Particular arrangements of the secondary attachment means can be constructed to provide a Peripheral Release value which is not more than about 1%, and optionally is not more than about 0.5% to provide improved performance. A suitable technique for determining the Peripheral Release value is Gel Containment Testing Method which is set forth in detail in the EXAMPLES section hereinbelow.

In an example of the invention, secondary attachments 122 can be provided by lines of substantially water-insoluble adhesive. Suitable adhesives include 34-5541, a synthetic rubber-based hot melt adhesive which is available from National Starch and Chemical Company, a business having offices in Bridgewater, New Jersey. The attachment lines have a width of about 0.2 cm, and can include lines which are positioned between adjacent pocket regions 108 and spaced from each of the adjacent pockets by a distance of at least about 0.1 cm.

Absorbent laminate 112 has a bodyside surface 116 and an outer side surface 118, and particular aspects of the invention can include a distribution layer 120 positioned adjacent the outer side surface of absorbent laminate 112. Alternatively, the distribution layer can be located adjacent the bodyside surface of the absorbent laminate. Optionally, a pair of distribution layers 120 and 184 (FIG. 8) can be positioned to sandwich absorbent laminate 112 therebetween, with a distribution layer on both the outer side and bodyside of the absorbent laminate. In further arrangements of the invention, any or all of the distribution layers 120 can be configured to provide a secondary absorbent body which supplements the ability of diaper 10 to contain absorbed liquids.

Distribution layer 120 can comprise a substantially unbonded mass of hydrophilic material, such as cellulosic fibers. The cellulosic fibers may, for example, be composed of wood pulp fluff, creped wadding, paper toweling, or the like. Distribution layer 120 can alternatively be provided by nonwoven webs comprising hydrophilic fibers, such as hydrophilic fibers composed of polyester, polypropylene, polyethylene, cotton, and the like.

In other arrangements of the invention, distribution layer 120 can comprise one or more layers of nonwoven fabric material comprising nonwoven bonded webs. The fibers may be composed of polyester, polypropylene, polyethylene, cotton, and the like. The webs may be bonded by various mechanisms, such as spunbonding, thermal bonding, through-air bonding, ultrasonic bonding, infrared bonding, adhesive bonding, and the like.

Distribution layer 120 can extend over an area which is not less than about 50 percent of the area covered by absorbent laminate 112. Alternatively, the distribution layer area is not less than about 70 percent, and optionally, is not less than about 90 percent of the absorbent laminate area to provide desired performance. In other arrangements of the invention, the area extent of distribution layer 120 is not more than about 300 percent of the projected surface area of absorbent laminate 112. Alternatively, the distribution layer area is not more than about 200 percent, and optionally, is not more than about 150 percent of the absorbent laminate area.

In the various configurations of distribution layer 120, the distribution layer, with respect to its total weight, may contain about 0-20 weight percent of high absorbency material. Alternatively, the amount of high absorbency material within distribution layer 120 is not more than about 10 weight percent, and optionally, is not more than about 5 weight percent to provide desired benefits.

In the illustrated embodiment, for example, distribution layer 120 can comprise a matrix of hydrophilic fibers, such as a web of cellulosic fluff, mixed with particles of high-absorbency material. In particular arrangements, distribution layer 120 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the distribution layer, with lower concentrations toward the bodyside of the distribution layer and relatively higher concentrations toward the outer side of the distribution layer. Suitable z-gradient configurations are described in U.S. Pat. No. 4,699,823 issued Oct. 13, 1987 to Kellenberger et al., the disclosure of which is incorporated herein by reference to the extent that it is consistent with the present description. The superabsorbent particles may also be arranged in a generally discrete layer within the matrix of hydrophilic fibers. In addition, two or more different types of superabsorbent may be selectively positioned at different locations within or along the fiber matrix.

In particular arrangements of the invention, distribution layer 120 has a length and/or width which can be less or greater than a corresponding length and/or width of absorbent laminate 112. An arrangement wherein the length and/or width of the distribution layer is greater than the length and/or width of the absorbent laminate can provide a marginal boundary area of distribution layer 120 for capturing liquids which move past and beyond the terminal edges of absorbent laminate 112. In the illustrated embodiment, for example, distribution layer 120 has a length and/or width which is within the range of approximately 75-175 % of a corresponding length and/or width of absorbent laminate 112.

The high-absorbency material employed with the various aspects of the invention may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol ), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 micrometers to about 1 millimeter. "Particle size" as used herein means the weighted average of the smallest dimension of the individual particles.

In the various aspects of the invention, particular components of absorbent structure 32, such as absorbent laminate 112 and distribution layer 120, can include a quantity of high-absorbency material distributed therein. Selected superabsorbent polymers having improved absorbent properties can be important for maximizing the performance while retaining the desired thinness of the absorbent article.

In another aspect of the invention, the high absorbency material employed with absorbent laminate 112 exhibits an Absorbency Under Load (AUL) value of at least about 10 grams of liquid saline per gram of high absorbency material, as determined under a pressure of 0.9 psi (6.2 kPa). Alternatively, the high absorbency material exhibits an AUL value of at least about 15 grams per gram, and optionally, exhibits an AUL value of at least about 20 grams per gram to provide desired performance. As used herein, the Absorbency Under Load value of a particular superabsorbent material refers to the amount, in grams, of an aqueous solution of sodium chloride (0.9 weight percent sodium chloride) which 1 gram of superabsorbent material can absorb in 60 minutes while under a selected restraining load.

A particular example of a high absorbency material suitable for use in the present invention is FAVOR SAB 870 superabsorbent polymer produced by Stockhausen, Inc., a business having offices in Greensboro, North Carolina.

It has been discovered that the performance of a superabsorbent material relates to the ability of the superabsorbent material to absorb a liquid not only while under a single given restraining force, such as about 0.3 pound per square inch (about 2 kPa), but also over a broader range of restraining forces, such as about 0.01–0.9 pound per square inch (about 0.7–6.2 kPa). The ability of a superabsorbent material to absorb a liquid under a variety of different restraining pressures has, for the purposes of this application, been quantified as the Pressure Absorbency Index.

The Pressure Absorbency Index is the sum of the Absorbency Under Load values for a superabsorbent material determined under the following loads: 0.01 pound per square inch (0.07 kPa); 0.29 pounds per square inch (2.0 kPa); 0.57 pounds per square inch (3.9 kPa); and 0.90 pounds per square inch (6.2 kPa). That is, the Absorbency Under Load values for a given superabsorbent material are determined under the restraining forces set forth above according to the method set forth in the document identified below. The Absorbency Under Load values determined under the restraining loads set forth above are then totaled to determine the Pressure Absorbency Index.

Superabsorbent materials useful in the present invention have a Pressure Absorbency Index of at least about 100, particularly of at least about 105, more particularly of at least about 110, even more particularly of at least about 120; and most particularly of at least about 140.

Superabsorbent materials useful in the present invention may also suitably have a 16-hour extractables level, determined as set forth in the document identified below, of less than about 13 weight percent, particularly of less than about 10 weight percent, more particularly of less than about 7 weight percent, and even more particularly of less than about 3 weight percent.

Suitable techniques for determining the AUL value, Pressure Absorbency Index and extractables level of high absorbency material 110 are set forth in copending U.S. patent application Ser. No. 016,312; entitled "ABSORBENT COMPOSITE"; of M. Melius et al.; filed on Feb. 24, 1993 (Attorney Docket No. 10,838); and in its associated continuation-in-part application filed on even date herewith; the disclosures of which are hereby incorporated by reference to the extent that they are consistent herewith.

Where distribution layer 120 comprises particles of superabsorbent polymer distributed within a matrix of hydrophilic fibers, such as a layer of wood pulp fluff, the hydrophilic fibers and high-absorbency particles can be provided in a fiber-to-particle ratio which is not less than about 50:50, and desirably, is not less than about 80:20. This ratio is alternatively not less than about 90:10, and optionally, is not less than about 95:5, by weight, to provided desired performance. Such fiber-to-particle ratios can be particularly desireable in the target zone of the absorbent structure. In particular embodiments of the invention, the fiber-to-particle weight ratio is within the range of about 95:5 to 100:0 to provide desired performance.

For example, the invention can be configured to provide a medium-size article which has been referred to as a "Step 3" size diaper. Such articles can comprise a distribution layer 120 in the form of a fluff pad which includes 4–25 grams of wood pulp fluff. The pad can alternatively include about 5–20 grams of fluff, and can optionally include about 6–15 grams of fluff to provide desired benefits. The woodpulp fluff generally provides shape and form to diaper 10, and carries and positions the particles of superabsorbent polymer or other high-absorbency material. Distribution layer 120 can also contain about 0–12 grams of superabsorbent polymer, and in the shown embodiment, the distribution layer is substantially free of superabsorbent polymer.

The hydrophilic fibers and high-absorbency particles can be configured to form an average composite basis weight which is within the range of about 90–650 gsm. Again, such basis weight is particularly desireable in the target zone of the absorbent structure. In certain aspects of the invention, the average composite basis weight is within the range of about 110–550 gsm, and optionally is within the range of about 130–450 gsm to provide desired performance.

To provide the desired thinness dimension to the absorbent article, retention portion 48 is configured with a thickness which is not more than about 0.6 cm. Alternatively, the thickness is not more than about 0.53 cm, and optionally is not more than about 0.5 cm to provide improved benefits. For the purposes of the present invention, the thickness is determined under a restraining pressure of 0.2 psi (1.38 kPa).

The density of distribution layer 120 or other component of the absorbent article can be calculated from its basis weight and thickness. With respect to diapers, for example, the weight and thickness are measured with respect to samples taken from newly unpacked, unfolded and dry diapers at a restraining pressure of 0.2 psi (1.38 kPa). For measuring thickness, a suitable device is a TMI foam thickness gauge, Model No. TM1-49-21 or its equivalent. The apparatus is available from Testing Machines, Inc. of Amityville, New York.

The fluff and superabsorbent particles can be selectively placed into desired zones of distribution layer 120. For example, the fluff basis weight may vary across the width dimension of distribution layer 120. Alternatively, relatively larger amounts of fluff may be positioned toward the front waistband end of the distribution layer. For example, see U.S. Pat. No. 4,585,448 issued Apr. 29, 1986, to K. Enloe.

In the illustrated embodiment, the majority of the superabsorbent material can be distributed down a medial region of distribution layer 120 which extends along the length dimension of the retention portion and measures about 1–10 inches (about 2.54–25.4 cm) in width. The medial region may optionally have a width within the range of about 1.5–4 inches (about 3.8–10.2 cm). In addition, the superabsorbent material may have a selected zoned placement to reduce the amount of superabsorbent material located proximate the side and end edges of the distribution layer. The reduced amounts of superabsorbent material at the edges of the distribution layer can help improve the containment of the superabsorbent particles within the fibrous fluff matrix of distribution layer 120. The pulsed, zoned placement of the superabsorbent material can, for example, be achieved by the method and apparatus described in copending U.S. patent application Ser. No. 07/462,363 of C. Pieper et al. filed Jan. 9, 1990, and entitled "Method and Apparatus for Intermittently Depositing Particulate Material in a Substrate" (Attorney Docket No. 8761), the disclosure of which is hereby incorporated by reference to the extent that it is consistent herewith.

In a particular aspect of the invention, absorbent structure 32 is generally T-shaped with the laterally extending cross-bar of the "T" generally corresponding to the front waistband portion of the absorbent article for improved performance, especially for male infants. In the illustrated embodiments, the retention portion across the ear section of the front waistband region of the article has a cross-directional width of about 9 inches (about 23 cm), the narrowest portion of the crotch section has a width of about 3.5 inches (about 8.9 cm) and the back waistband region has a width of about 4.5 inches (about 11.4 cm).

With reference to FIGS. 2 and 4, the entire absorbent structure 32, or any individual portion thereof, such as distribution layer 120, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to other components of the product construction.

Absorbent wrap 70 typically comprises a single layer of wrapsheet material. Optionally, the wrap may comprise a multi-element wrapsheet which includes a separate bodyside wrap layer 71 and a separate outer side wrap layer 73, each of which extends past all or some of the peripheral edges of retention portion 48. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, the bodyside and outer side layers of absorbent wrap 70 extend at least about 0.5 inch (about 1.27 cm) beyond the peripheral edges of the retention portion to provide an outwardly protruding, flange-type bonding area over which the periphery of the bodyside portion of the absorbent wrap may be completely or partially connected to the periphery of the outer side portion of the absorbent wrap.

The bodyside and outer side layers of a multi-element wrap sheet 70 may be composed of substantially the same material, or may be composed of different materials. For example, the outer side layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity.

To provide the bonding between the bodyside and outer side portions of absorbent wrap 70, an adhesive, such as National Starch 33-9156 adhesive (a polyvinylacetate-based emulsion), can be printed onto the appointed bonding areas 74 of the absorbent wrap with, for example, a rotogravure-type system. Rotogravure-type adhesive applicators are available from Egan Machinery Division, a business having offices at Oconto Falls, Wisconsin. Retention portion 48 can then be placed between the bodyside and outer side portions of absorbent wrap 70 and the mating edges of the absorbent wrap portions can be bonded together to provide a generally complete peripheral seal along substantially the entire perimeter of retention portion 48.

Due to the thinness of retention portion 48 and the high superabsorbent concentrations within the retention portion, the liquid uptake rates of the retention portion, by itself, may be too low, or may not be adequately sustained over three insults of liquid into the absorbent structure. The addition of a layer of surge management material into the absorbent structure, however, can advantageously improve the overall uptake rate of the composite absorbent structure. Surge management portion 46 is typically less hydrophilic than retention portion 48, and has an operable level of density and basis weight to quickly collect and temporarily hold liquid surges, and to transport the liquid from its initial entrance point to selected regions of absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web composed of natural and synthetic fibers. The surge management portion may be composed of a substantially hydrophobic material, and the hydrophobic material may optionally be treated with a surfactant or otherwise processed to impart a desired level of wettability and hydrophilicity.

In addition, the surge management layer can be configured with an average bulk density which is not more than about 0.10 g/cc, determined at 0.2 psi (1.38 kPa). Alternatively, the bulk density of the surge management layer is within the range of about 0.02–0.06 g/cc to provide improved effectiveness. The types of nonwoven materials that may be employed include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0–3.0 inch (about 2.54–7.62 cm).

Surge management portion 46 can have a generally uniform thickness and cross-sectional area. Alternatively, a configuration can be employed wherein the bodyside surface area of the surge management portion is greater or less than the surface area of a section taken along an X-Y plane located below the bodyside surface of the surge management portion.

With reference again to FIGS. 1, 2 and 4, the absorbent article represented by diaper 10 can generally comprise a liquid surge management portion 46 and an absorbent retention portion 48 adjacently arranged in direct, contacting liquid communication with the surge management portion. In the illustrated embodiment, for example, the surge management portion is positioned on the body side of absorbent laminate 112. Optionally, the surge management portion may be positioned on the outer side of the absorbent laminate. As representatively shown in FIGS. 2 and 4, respectively, surge management portion 46 may alternatively be configured for placement adjacent an inwardly facing, bodyside of topsheet 28, or adjacent an outer side of the topsheet.

In the various embodiments of the invention, at least a part of surge management portion 46 is located within target zone 53, and in particular arrangements, the surge management portion has an areal extent which extends completely over target zone 53. Retention portion 48 is positioned in liquid communication with surge management portion 46 to receive liquids released from the surge management portion and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to eventually release such liquids into the layer or layers comprising retention portion 48.

The layer comprising the surge management portion is substantially free of absorbent gelling material. Surge management portion 46 may, however, contain a very small amount of gelling material to help acquire an initial liquid surge, but the amount should not be excessive. When excessive amounts of absorbent gelling material are maintained in surge management portion 46, however, the gelling material can cause the structure to retain and hold unacceptably high amounts of the liquid. In addition, the transport of liquids away from target zone 53 to other sections of absorbent structure 32, particularly retention portion 48, can be undesirably impaired.

As mentioned previously, surge layer 46 can be a separately formed layer, which lies adjacent the outerwardly facing surface of topsheet 28 between the retention portion and topsheet. Thus, surge management portion 46 need not extend through the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in the generally sideways (X-Y) direction.

A capillary force differential can be provided at the interface between the retention portion 48 and the material immediately adjacent the bodyside of the retention portion to improve the containment characteristics of absorbent structure 32. For example, if the surge management portion 46 is a layer positioned immediately adjacent to the retention portion, and if the surge layer is appropriately configured to provide and maintain a relatively lower capillary attraction, as compared to the capillary attraction exhibited by retention portion 48, then liquid surges occurring in target zone 53 tend to be desorbed more readily from the surge management portion and into the retention portion. Because retention portion 48 can thereby have a relatively higher capillarity than surge management portion 46, the liquid surges tend to be drawn into retention portion 48 and distributed to the more remote regions thereof by wicking along the plane generally defined by the retention portion.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, the surge management portion can be generally rectangular-shaped with a top surface area within the range of about 15–102 in$^2$ (about 97–660 cm$^2$). In the shown embodiment, surge layer 46 has a top surface area of about 68 square inches (about 440 cm$^2$).

In the various embodiments of the invention, such as the arrangement of FIG. 4 where surge management portion 46 is interposed between topsheet 28 and retention portion 48, the surge management portion can comprise a nonwoven fabric which has a basis weight within the range of about 17–102 gsm and includes at least about 25 wt % of bicomponent fibers to provide a desired bicomponent fiber bond-matrix. Up to 100% of the surge fabric can be composed of bicomponent fibers, and accordingly, 0–75 wt % of the fabric may comprise non-bicomponent fibers. In addition, the fabric can comprise a blend of smaller diameter fibers and relatively larger diameter fibers. The smaller sized fibers have a denier of not more than about 3 d, and alternatively have a denier within the range of about 0.9–3 d to provide desired benefits. The larger sized fibers have a denier of not less than about 3 d, and optionally have a denier within the range of about 3–18 d to provide desired performance. The lengths of the fibers employed in the surge management materials are within the range of about 1–3 in (about 2.54–7.62 cm). The bond-matrix and the blend of fiber deniers can advantageously provide for and substantially maintain a desired pore size structure.

For example, the surge management portion may comprise a nonwoven fibrous web which includes about 75 percent polyester fibers of at least 6 denier, such as PET (polyethylene terephthalate) fibers available from Hoechst Celanese, a business having offices at Charlotte, North Carolina. The polyester fibers have a length ranging from about 1.5–2.0 inches (about 3.8–5.1 cm) in length. The remaining 25 percent of the fibrous web can be composed of bicomponent binder fibers which are not more than 3 denier, and in the shown embodiment, are about 1.5 denier. The bicomponent fiber length ranges from about 1.5–2 inches (about 3.8–5.1 cm). Suitable bicomponent fibers can, for example, be a wettable polyethylene/polypropylene bicomponent fiber, available from Chisso, a business having offices located in Osaka, Japan. The bicomponent fiber can be a composite, sheath-core type with the polypropylene forming the core and polyethylene forming the sheath of the composite fiber. The polyester fibers and bicomponent fibers are generally homogeneously blended together and are not in a layered configuration. The fibers can be formed into a carded web which is thermally bonded, such as by through-air bonding or infrared bonding. As another example, the surge management portion may be composed of a bonded carded web which has a basis weight of about 50 gsm and includes a mixture of polyester (PET) single-component fibers and PET/polyethylene bicomponent fibers. The PET fibers comprise about 60 wt % of the nonwoven fabric, and are about 6 denier with an average fiber length of about 2 in (about 5.1 cm). The PET/polyethylene bicomponent fibers comprise about 40 wt % of the fabric, and are about 1.8 denier with an average fiber length of about 1.5 in (about 3.8 cm). The PET forms the core and the polyethylene forms the sheath of the fiber. In optional constructions, the larger-sized, PET single-component fibers may be replaced by bicomponent fibers. In further optional arrangements, polypropylene/polyethylene bicomponent fibers may be employed to form the bicomponent fiber portion of any of the described fabrics. In addition, the bicomponent fibers may be flat crimped or helically crimped.

Referring to FIG. 2, surge management portion 46 can be advantageously configured for placement against the bodyside of topsheet 28. Accordingly, an outerward major surface of the surge management portion would be immediately adjacent and contact the topsheet, and the opposite, innerward major surface of the surge management portion would contact the skin of the wearer. In the shown embodiment, backsheet 30 defines a front waistband section 12, a rear waistband section 14, and an intermediate or crotch section 16 interconnecting the front and rear waistband sections. The backsheet has predetermined width and length dimensions, and an absorbent body 32 is superposed on the backsheet. Topsheet layer 28 is disposed in facing relation with the absorbent body to generally sandwich the absorbent body between the backsheet and topsheet layers, and the topsheet has an appointed outer side surface and an appointed bodyside surface. A width dimension of topsheet 28 is configured to extend completely over the width of the absorbent body in at least a portion of the crotch section of the absorbent body. With the shown embodiment, the topsheet is also substantially coextensive with the backsheet width over at least a portion of the backsheet crotch section. A surge management portion, such as surge layer 46, is located on the bodyside surface of the topsheet layer, with the surge layer having a width dimension which is less than the width of said topsheet layer.

Where surge management portion 46 is configured for placement adjacent the bodyside of topsheet 28, the surge management portion can be a composite, liner-surge web 76. The composite web can include a bodyside layer portion and an outer side layer portion. The layer portions can be separately laid and can have different structures and compositions. The fibers within each layer and the intermingling fibers between the layer portions are then suitably interconnected (such as by powder bonding, point bonding, adhesive bonding, latex bonding, or by through-air or infrared thermal bonding) to form a composite web. The resultant composite web has a total basis weight of not more than about 102 gsm. Alternatively, the total basis weight is within the range of about 24–68 gsm, and optionally is within the range of about 45–55 gsm. In addition, the total average density of the composite web is not more than about 0.10 g/cc, and optionally is not more than about 0.05 g/cc, as determined at 0.2 psi (1.38 kPa).

The outer side, surge layer has a basis weight within the range of about 17–50 gsm and includes at least about 25 wt % of bicomponent fibers to provide a desired bicomponent fiber bond-matrix. The outer side layer also comprises a blend of smaller diameter fibers and relatively larger diameter fibers. The smaller sized fibers have a denier within the range of about 0.9–3 d, and the larger sized fibers have a denier within the range of about 3–15 d. The bond-matrix and the blend of fiber deniers can advantageously provide for and substantially maintain a desired pore size structure within the outer side layer.

For example, the outer side layer may be composed of a carded web which has a basis weight of about 34 gsm and includes a mixture of polyester (PET) single-component fibers, available from Hoechst-Celanese, and polyethylene/PET (PE/PET) sheath-core bicomponent fibers, available from BASF Corp., Fibers Division, a business having offices in Enka, North Carolina. The PET fibers can comprise about 60 wt % of the outer side layer and have a denier of about 6 with an average fiber length of about 2 in (about 5.1 cm). The polyethylene/PET bicomponent fibers comprise about 40 wt % of the outer side layer, and have a denier of about 1.8 with an average fiber length of about 1.5 in (about 3.8 cm). Optionally, the larger-sized, PET single-component fibers may be replaced by bicomponent fibers. As a further option, polyethylene/polypropylene (PE/PP), sheath-core bicomponent fibers may be employed to form the bicomponent fiber portion of any of the described fabrics. Suitable PE/PP bicomponent fibers are available from Chisso Corp., a business having offices in Osaka, Japan.

The bodyside, liner layer includes at least about 90 wt %, and preferably 100 wt %, of bicomponent fibers to provide desired levels of tactile softness and abrasion resistance. The bodyside layer has a basis weight of at least about 10 gsm, and the bicomponent fiber size is within the range of about 0.9–3 denier with a fiber length within the range of about 1–3 in (about 2.54–7.62 cm). Alternatively, the fiber denier is within the range of about 1.5–2.5, and optionally, is about 1.8 denier. A preferred fiber length is about 1.5 in (about 3.8 cm). For example, bodyside layer 80 may comprise a carded web which has a basis weight of about 17 gsm and is composed of 100% PET/polyethylene, sheath-core bicomponent fibers, obtained from BASF Corp., with a fiber denier of about 1.8 and fiber lengths of about 1.5 in (about 3.8 cm).

In a particular embodiment of the composite surge management portion, the outer side layer forms approximately 65 weight percent of the composite web and is composed of a blend of polyester fibers and bicomponent fibers. With respect to this blended outer side layer, about 60 weight percent of the blended layer is composed of polyester fibers of at least about 6 denier and with a fiber length within the range of about 1.5-2 inches (about 3.8–5.1 cm). The remaining 40 percent of the blended layer is composed of bicomponent fibers of not more than about 3 denier, and preferably about 1.8 denier, with fiber lengths within the range of about 1.5–2 inches (about 3.8–5.1 cm). The bodyside layer 80 comprises the remaining 35 weight percent of the composite web, and is composed of bicomponent fibers having a denier within the range of about 0.9–3 to provide a soft liner type material appointed for placement against a wearer's skin. In a particular embodiment, the bodyside layer of the composite web has a basis weight of about 15 gsm and is composed of bicomponent fibers of about 2 denier.

Another embodiment of the composite web can comprise a bodyside layer composed of about 100% polyethylene/polyester sheath-core bicomponent fibers of not more than about 3 denier. The bodyside layer has a basis weight of about 15 gsm. In addition, this embodiment of the composite web includes an outer side layer composed of a 50/50 blend of polyester fibers of about 6 denier and polyester/polyethylene, sheath-core bicomponent fibers of not more than about 3 denier.

In the various embodiments of the invention, the surge layer width is within the range of about 16–100 % of the topsheet width. The surge layer width is alternatively at least about 24% of the topsheet width, and optionally, is at least 50% of the topsheet width to provide desired levels of effectiveness.

The various embodiments of surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within front section 49 of absorbent structure 32. Thus, surge management portion 46 can be approximately centered about the longitudinal center line 58 of absorbent structure 32, and positioned primarily in central region 54 of front section 49 of absorbent structure 32. In the illustrated embodiment, none of surge management portion 46 is located in ear regions of 50 and 52.

The generally forward, offset positioning of surge management portion 46 can be defined by specifying the percentage of the top surface area of surge management portion 46 which is found forward of a particular reference point, such as transverse centerline 24, along the length of absorbent structure 32. The positioning of surge management portion 46 can alternatively be defined with respect to the volume or weight percent of the surge management portion which is positioned forward of a reference point.

The surge management portion and the topsheet layer each have an effective average pore size. In constructions where the surge management portion is located adjacent the outer side of the topsheet, the effective average pore size of the surge management material is preferably smaller than the effective average pore size of said topsheet material, and the material of the surge management portion is preferably more hydrophilic than the topsheet material.

With the various embodiments of the invention, the basis weight of surge management portion 46 is at least about 24 grams per square meter (gsm), alternatively is at least about 40 gsm, and optionally is at least about 45 gsm to help provide the total void volume capacity desired for effective operation. In a particular aspect of the invention, the basis weight is not more than about 300 gsm, alternatively, is not more than about 150 gsm, and optionally, is not more than about 100 gsm to provide desired advantages. In a further aspect of the invention, the surge management portion has a basis weight which is within the range of about 40–60 gsm, and optionally, is within the range about 45-55 gsm to provide improved effectiveness. In a particular embodiment, the basis weight is about 50 gsm.

The amount of basis weight can be important for providing a total holding capacity which is adequate to temporarily retain the amount of liquid that is typically discharged by a wearer during a single surge/insult of liquid into the absorbent article. For instance, a basis weight which is too low can result in excessive pooling of liquid against the wearer's skin or excessive run-off of liquid. It will be readily apparent that absorbent articles requiring more surge capacity may also require proportionally greater amounts of surge management material.

The surge management material, however, need not be of uniform basis weight throughout its areal extent, but instead can be arranged so that some sections have more surge management material compared to other sections. For the purposes of the present invention, the effective basis weight will be the weight of the surge management material divided by the area over which the surge management portion extends.

The following Examples are presented to provide a more detailed understanding of the invention. The Examples are intended to be representative, and are not intended to specifically limit the scope of the invention.

EXAMPLES

Delamination Testing Procedure

The laminate composites were tested for delamination, attachment strength on a computerized tensile testing machine. Suitable machines include, for example, a Sintech brand tensile tester which is equipped with a 22N maximum force load cell and is accurate to ±0.005N. The sample holders or "jaws" are configured to be at least as wide as the widest sample being tested. Sintech is a business having offices in Stoughton, Massachusetts. Equivalent testing instruments are available from other manufacturers.

The procedure was based on the ASTM Standard Test Method for Peel Resistance of Adhesives ("T-Peel Test); Designation: D 1876-93, approved Jan. 15, 1993. The procedure was modified as follows:

| | |
|---|---|
| § 4.1.1 | Some of the specimens had a maximum load less than 15% of the upper limit of the loading range. |
| §§ 4.2 & 6.1 | Materials were conditioned for at least 2 days under the conditions specified; however, they were tested at laboratory conditions of 22 ± 2° C. and a relative humidity of 50 ± 20%. Materials were tested within 2 hours of being removed from the conditioning room. |
| § 5.2 | Unless otherwise specified, samples were cut into 102 mm wide test specimens, consistent with Note 6 in the ASTM procedure. |
| § 5.3 | The number of samples for each code is as given in the data tables. |
| § 7.1 | Head speed of 300 mm/minute was used. |
| § 7.3 | Testing was done to a 60 mm length. The peak force was recorded in Newtons. The peak force is then divided by the width of the test sample to provide force per unit width (N/cm). |
| Note 10 | Peak strength, energy, and average load were all recorded. Note that average peel strength will have little meaning in cases where the sample tears rather than delaminates. |

Samples were tested "dry", or "wet" with distilled water, or wetted with "saline" solution (0.85 % sodium chloride in water), as indicated in the tables below. The "wet" and "saline" samples were mounted in the jaws of the test instrument while dry, and were then sprayed with the water or saline (1 to 3 grams) using a hand-held spray bottle. 30 seconds after the last spray, the samples were tested.

EXAMPLES 1-8

Sample Preparation Procedure

Samples were prepared using assembly techniques consistent with U.S. Pat. No. 4,055,180 issued Oct. 25, 1977 to Karami (see, for example, column 3, line 26 and following). Polyethylene film (0.18 mm thick, 40 gsm) and conventional cellulose tissue (17 gsm) were cut into 127 mm×305 mm sections. The tissue was fused to the polyethylene film using a Vertrod Corp. Thermal Impulse Heat Sealing Machinery Model 8MG-3/4 heat sealing apparatus.

Figure 9:
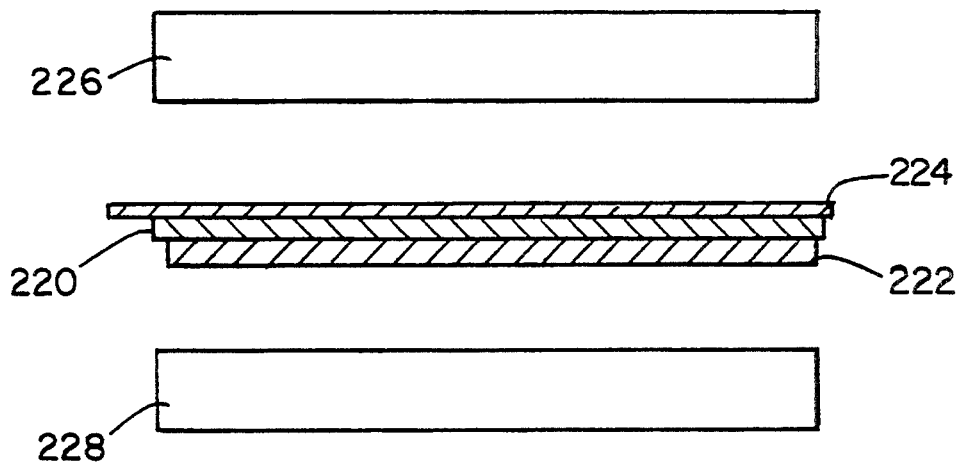
FIG. 9 representatively shows the use of a heat sealing unit to form pockets regions in an absorbent laminate.

As representatively shown in FIG. 9, polyethylene sheet 220 was placed over the tissue sheet 222. A silicone treated release paper 224 covered the polyethylene film to prevent sticking to the unheated bar 226 of the heat sealing unit. The heated bar 228 was arranged to contact t issue 222.

Temperature and dwell time settings were set to achieve an operable bond and seal. Temperature and dwell time settings which were too high melted through the polyethylene sheet. Settings which were too low did not strongly bond the materials. In the examples, the temperature was set at "7", and a dwell time of approximately 2 seconds was used for bonding.

A series of eight seal lines were made across the width of the tissue/polyethylene to bond the materials together. Each of the seal lines was 17 mm±4 mm wide, and the seal lines were about 16 mm apart, center to center. A longitudinal fusion line was made along one long edge of the sheets to form seven slots. Into each of these slots was placed 0.25±0.01 gram of FAVOR 870 polyacrylate superabsorbent. The slots were sealed with another longitudinal line, leaving a 16 mm gap between the lines, thereby creating seven pockets and leaving seven new slots. The process was then repeated twice more to provide an absorbent laminate structure having 21 pockets, with each pocket containing approximately 0.25 grams of superabsorbent.

Prior to testing, the absorbent laminate was cut longitudinally to provide three strips, with each strip measuring approximately 4.2 cm in width and including seven pockets of superabsorbent. The test data below are based on these 4.2 cm wide laminates Except as specified otherwise, the term "delamination" indicates that the carriers separated along the bonding line.

Results

Peel Testing of Heat Sealed Poly/Tissue Composites

| Sample | Condition | Peak Force (Newtons) | Force per unit width (N/cm) | Observations |
|---|---|---|---|---|
| 1 | dry | 1.04 | 0.25 | Delamination, NO tearing. |
| 2 | dry | 0.73 | 0.17 | Delamination, NO tearing. |
| 3 | dry | 0.69 | 0.16 | Some delamination, also tissue DID tear. |
| 4 | dry | 0.27 | 0.06 | Some delamination, also tissue DID tear. |
| 5 | dry | 0.24 | 0.06 | Some delamination, also tissue DID tear. |
| 6 | dry | 0.39 | 0.09 | Some delamination, also tissue DID tear. |
| 7 | dry | 0.55 | 0.13 | Delamination, NO tearing. |
| 8 | dry | 0.32 | 0.08 | Delamination, NO tearing. |
| 9 | dry | 0.20 | 0.05 | Some delamination, also tissue DID |

-continued

Peel Testing of Heat Sealed Poly/Tissue Composites

| Sample | Condition | Peak Force (Newtons) | Force per unit width (N/cm) | Observations |
| --- | --- | --- | --- | --- |
| 10 | dry | 0.32 | 0.08 | tear. Some delamination, also tissue did tear. |
| 11 | saline | 0.26 | 0.06 | Slight delamination, tissue DID tear. |
| 12 | saline | 0.23 | 0.05 | Some delamination, also tissue DID tear. |
| 13 | saline | 0.16 | 0.04 | Slight delamination, tissue DID tear. |
| 14 | saline | 0.19 | 0.05 | Some delamination, also tissue DID tear. |
| 15 | saline | 0.12 | 0.03 | Delamination, NO tearing. |
| 16 | saline | 0.23 | 0.06 | Slight delamination, tissue DID tear. |

Conclusion

Samples prepared in a manner consistent with Karami (U.S. Pat. No. 4,055,180), resulted in composites which had either insufficient wet strength or had carrier sheets which tore when wet. Samples 1–10 show sufficient dry strength, but samples 11–14 and 16 tore rather than delaminated when wet. Sample 15 had insufficient wet strength.

EXAMPLES 17–22

Sample Preparation Procedure

Figure 10:
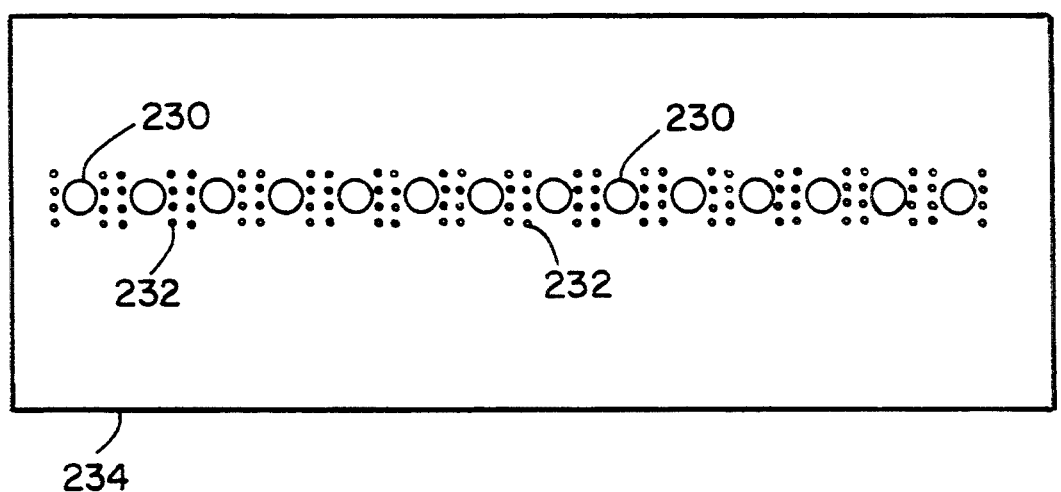
FIG. 10 representatively shows the use of an embossing die employed to form pockets regions in an absorbent laminate.

A metal die was prepared to simulate one section of the embossing roll described in U.S. Pat. No. 4,414,255 issued Nov. 8, 1993 to Tokuyama (see, for example, column 5, lines 3–17). As representatively shown in FIG. 10, 55 mm×118 mm aluminum plate was constructed with a multiplicity of holes 230 and pins 232. Fourteen, 2.6 mm diameter holes were drilled into the plate. The holes 230 were aligned, and were spaced with a 5.2 mm, edge-to-edge distance between each hole. Eight 0.5 mm diameter steel pins 232 were mounted around each of the holes, with four pins located at each of two opposed sides of each hole. Accordingly, eight pins were located between adjacent holes. The pins were located with a 1.25 mm center-to-center distance between pins, and protruded 0.4 mm above the surface of the plate. The entire embossing pattern measures 4 mm×71 mm. The die was heated in a forced air oven at 160° C. oven for 30 minutes prior to use.

Favor 870 superabsorbent polymer (SAP) was sieved to remove particles larger than 300 micrometers. A 60 mm×120 mm swatch of conventional cellulose tissue (27 gsm) was evenly sprinkled with the SAP at a distribution of 20 gsm. A second sheet of cellulose tissue was then placed over the SAP. Six samples were prepared using this method. The tissue/SAP/tissue combination was placed on a polytetrafluoroethylene (PTFE) coated surface.

Three samples were treated as follows, employing a method consistent with that of the Tokuyama patent:

(a) The die was removed from the oven and pressed into the tissue/SAP/tissue combination using a force of 400 Newtons (N) for one second. This force is equivalent to the weight applied by 5.7 kg per centimeter of length of the embossing pattern. This procedure was repeated 3 times.

The remaining three samples were treated in the following manner, employing a pressure which exceeded the pressure given in Tokuyama:

(b) The die was removed from the oven and pressed into the tissue/SAP/tissue combination using a force of 20,000N for one second. This force is equivalent to the weight applied by 290 kg per centimeter of length of the embossing pattern. This procedure was repeated 3 times.

Results

Using both pressing procedures, the resultant composite was very weakly bonded.

Following procedure (a), the bonds were so fragile that the composite could not be lifted off the PTFE surface without delaminating. The mass of one ply of tissue plus the superabsorbent was 0.34 g. The gravitational force tending to delaminate the sample as it was lifted off the PTFE sheet was 0.03N.

Following procedure (b), the bonds were marginally stronger, but the composite could not be mounted in the jaws of the test apparatus without delaminating. The delamination strength was not more than 0.3N.

Conclusion

Samples prepared in a manner consistent with "Example 1" of Tokuyama (U.S. Pat. No. 4,414,255) resulted in very weakly bonded composites; with dry peel strength substantially less than is desired for the invention.

EXAMPLES 23–91

Sample Preparation Procedure

Figure 11:
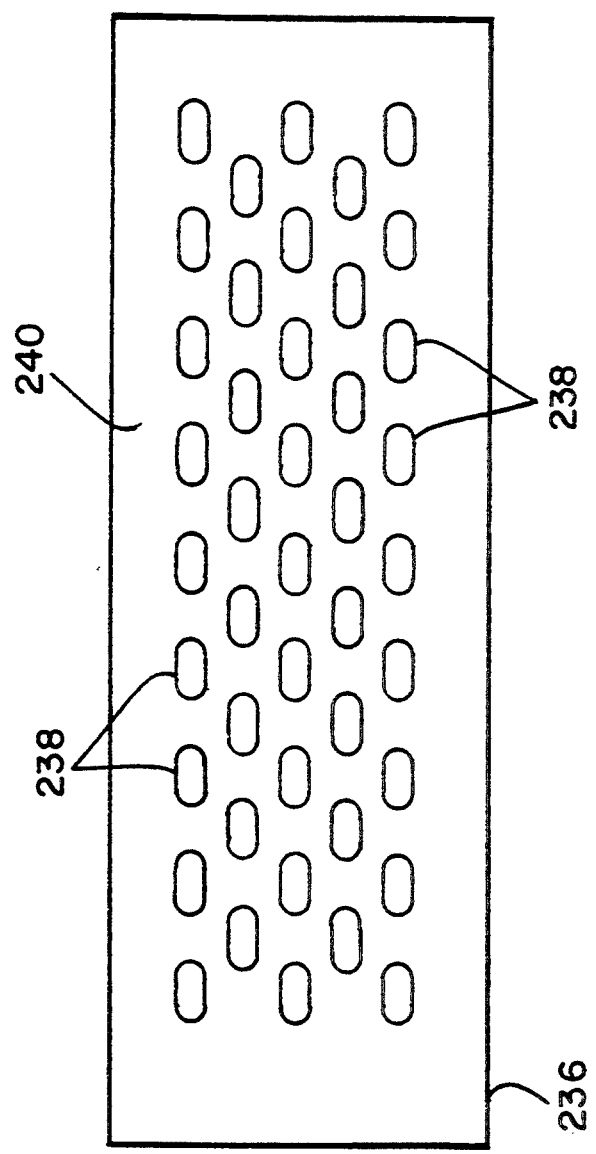
FIG. 11 representatively shows a top view of a vacuum box employed to form particular arrangements of the invention.

A vacuum box 236 was prepared with a multiplicity of holes 238 formed on the top member 240 and arranged as representatively shown in FIG. 11. Each elongate slot 238 measured approximately 25 mm×12 mm. The overall pattern measured 260 mm×87 mm. The longer dimension of the slots were aligned along the length of the sample, and the length of sample corresponds to the length 90 of the article in which the sample could be incorporated. Along the length dimension of the pattern, the rounded ends of the immediately adjacent slots were spaced apart by a distance of 6–7 mm, and along the width of the sample, the straight sides of the immediately adjacent slots were spaced apart by a distance of 6–7 mm.

Samples were prepared by placing a first carrier sheet onto the vacuum box. Three types of substrates, i.e., carrier sheet layers, were used: 10 gsm, Hydrofil® meltblown; 111 gsm hydro-entangled pulp made with Kimberly-Clark Corp., Long Lac 19 northern softwood pulp; and 23 gsm cellulosic forming tissue. Hydrofil® is a hydrophilic amide-cooethylene oxide copolymer material available from Allied-Signal Corporation a business having offices in Morristown, New Jersey. The carrier sheets were cut into 127 mm×305 mm rectangles, with the machine direction of the tissue or nonwoven being the same as the long direction of the rectangle; additionally, the forming tissue was cut in the cross machine direction, giving a total of four carrier sheets.

The vacuum was turned on, and 5 grams of SAP (superabsorbent polymer) were uniformly dispersed onto a first carrier sheet. Favor 870 polyacrylate SAP was used for this experiment. Using a small brush, superabsorbent was swept into the areas of the first carrier sheet over the hole regions.

Adhesive was sprayed onto the superabsorbent/carrier composite. The adhesives included National Starch and Chemical Company 34-5541 (hot melt construction adhesive), 70-3998 (Cycloflex, hot melt water sensitive adhesive), and 33-2058 (poly vinyl acetate emulsion adhesive) were used. The hot melt adhesives were applied using a hand operated spray gun, such as a PAM 600 Spraymatic spray gun available from Fastening Technology, Inc., a business located at Charlotte, North Carolina. The emulsion adhesive was diluted to 10% solids (by weight) and applied with a hand-powered spray bottle. The dry mass of adhesive was 0.8±0.3 grams. A second carrier sheet, of the same type as the first, was placed over the adhesive, and then pressed into place by rolling a cylinder across the surface. The cylinder weighed about 1 kg and was 5 cm in diameter and 5 cm in length.

In some cases where it was difficult to delaminate a sufficient length of the composite to place in the Sintech's jaws, a hot air gun was used to warm the end of the composite and loosen the bonds sufficiently to have enough material for the jaws to grab. For some samples a few drops of water effectively opened the ends of the sheets, the ends of these composites were then dried with the hot air gun before testing. All samples which required the use of a hot air gun were allowed to cool to room temperature before testing.

In the following tables and charts, the terms listed below have the following meanings:

"Hydrofil"—carrier layers composed of meltblown nonwoven fabric constructed with Hydrofil copolymer and having a basis weight of 10 gsm.

"Machine"—carrier layers composed of cellulose tissue; sample tested in the machine-direction with the length of the sample oriented in the direction in which the tissue was manufactured.

"Cross"—carrier layers composed of cellulose tissue; sample tested in the cross-machine direction with the length of the test sample oriented at right angles to the direction in which the tissue was manufactured.

HEP—carrier layers composed of hydroentangled pulp, as described herein.

EXAMPLES 23–45

| Peel Testing Results for Samples Bonded with 70-3998: | | | | | |
|---|---|---|---|---|---|
| Sample | Carrier | Condition | Force, Newtons | Force per unit width, N/cm | Mode of Failure |
| 23 | Hydrofil | dry | 2.10 | 0.207 | Tear. |
| 24 | Hydrofil | water | 1.16 | 0.114 | Tear. |
| 25 | Machine | dry | 5.93 | 0.584 | Tear. |
| 26 | Machine | dry | 4.00 | 0.394 | Tear. |
| 27 | Machine | dry | 5.69 | 0.560 | Tear. |
| 28 | Machine | dry | 7.12 | 0.701 | Tear. |
| 29 | Machine | water | 0.69 | 0.068 | Delamination, NO tearing. |
| 30 | Machine | water | 0.88 | 0.087 | Delamination, slight tearing. |
| 31 | Machine | water | 1.37 | 0.135 | Delamination, slight tearing. |
| 32 | Machine | water | 1.33 | 0.131 | Delamination, slight tearing. |
| 33 | Cross | dry | 1.38 | 0.136 | Tear. |
| 34 | Cross | dry | 4.76 | 0.469 | Tear. |
| 35 | Cross | dry | 2.93 | 0.288 | Tear. |
| 36 | Cross | water | 0.98 | 0.096 | Delamination, NO tearing. |
| 37 | Cross | water | 0.49 | 0.048 | Delamination, NO tearing. |
| 38 | Cross | water | 0.55 | 0.054 | Delamination, NO tearing. |
| 39 | HEP | dry | 9.83 | 0.968 | Delamination, NO tearing. |
| 40 | HEP | dry | 3.09 | 0.304 | Delamination, NO tearing. |
| 41 | HEP | dry | 8.34 | 0.821 | Delamination, NO tearing. |
| 42 | HEP | dry | 2.09 | 0.206 | Delamination, NO tearing. |
| 43 | HEP | water | 2.20 | 0.217 | Delamination, NO tearing. |
| 44 | HEP | water | 1.85 | 0.182 | Delamination, NO tearing. |
| 45 | HEP | water | 3.84 | 0.378 | Delamination, NO tearing. |

Conclusions Based on 70-3988 Results

Samples prepared with 70-3998 (Cycloflex) adhesive varied in their wet and dry bond strengths according to the substrates used for testing.

The Hydrofil meltblown composite, Example 23, had sufficient dry strength. When wet, the carrier sheet of Example 24 was too weak relative to the bond strength of the adhesive so the composite tore rather than delaminated. Example 24 is not representative of the invention.

The composites of Examples 26–28, 33–35 and 39–42 all had sufficient dry strength for the subject invention. Examples 29, 36–38 and 43–45 are all exemplary of the invention. They had sufficient wet strength, yet delaminated without tearing. Examples 30–32 had sufficient wet strength, but exhibited some tearing of the wet carrier sheets. Accordingly, Examples 30–32 were marginally representative of the invention. It is believed that the examples had localized regions of high adhesive add-on or had localized regions of weakness in the carrier sheets.

The tissue based composites, tested both MD and CD, demonstrate the desired characteristics of the invention. That is, the bond was sufficiently strong when dry to hold the superabsorbent in place; however, when wet the bonds released. This will allow the superabsorbent to swell without rupturing the carrier.

The hydroentangled pulp sheets were sufficiently stronger than the adhesives, so that the dry composites delaminated rather than tore. By itself, this is acceptable.

A determination of a maximum wet delamination strength of the composite is ordinarily not required. The most desirable superabsorbents for this application have significant ability to swell against 0.9 psi (6.2 kPa). In the peel tests, a 10.2 cm wide sample was delaminated. The length of the composite being stressed at any given time was about 0.5 cm. The 6.2 kPa pressure applied to an area of 0.0005 m$^2$ (10 cm × 0.5 cm) yields a force of 3.1N, or 0.3N/cm across the width of the bond. This provides one estimate of an upper, acceptable wet delamination strength of the composite.

EXAMPLES 46–77

Peel Testing Results for Samples Bonded with 34-5541:

| Sample | Carrier | Condition | Force Newtons | Force per unit width N/cm | Mode of Failure |
|---|---|---|---|---|---|
| 46 | Machine | dry | 9.40 | 0.927 | Tear. |
| 47 | Machine | dry | 16.62 | 1.636 | Tear. |
| 48 | Machine | dry | 12.06 | 1.187 | Tear. |
| 49 | Machine | dry | 15.70 | 1.545 | Tear. |
| 50 | Machine | water | 5.86 | 0.577 | Initially slight tearing, then delamination. |
| 51 | Machine | water | 21.59 | 2.125 | Tear. |
| 52 | Machine | water | 2.92 | 0.287 | Delamination, slight tearing. |
| 53 | Machine | water | 1.72 | 0.169 | Delamination, slight tearing at edge. |
| 54 | Machine | water | 0.51 | 0.050 | Some delamination, also tissue DID tear. |
| 55 | Machine | water | 1.07 | 0.105 | Some delamination, also tissue DID tear. |
| 56 | Machine | water | 0.66 | 0.065 | Some delamination, also tissue DID tear. |
| 57 | Machine | water | 0.88 | 0.087 | Delamination, NO tearing. |
| 58 | Machine | saline | 0.55 | 0.054 | Delamination, NO tearing. |
| 59 | Machine | saline | 1.03 | 0.101 | Some delamination, also tissue DID tear. |
| 60 | Machine | saline | 0.78 | 0.077 | Some delamination, also tissue DID tear. |
| 61 | Machine | saline | 0.54 | 0.053 | Delamination, NO tearing |
| 62 | Cross | dry | 12.60 | 1.240 | Tear. |
| 63 | Cross | dry | 3.85 | 0.038 | Tear. |
| 64 | Cross | dry | 2.48 | 0.244 | Tear. |
| 65 | Cross | dry | 3.60 | 0.354 | Tear. |
| 66 | Cross | water | 5.58 | 0.549 | Tissue tore immediately at tape line. |
| 67 | Cross | water | 0.96 | 0.094 | Tissue tore imediately at tape line. |
| 68 | Cross | water | 2.56 | 2.252 | Tear. |
| 69 | Cross | water | 1.38 | 0.136 | Tear. |
| 70 | HEP | dry | 13.55 | 1.334 | Delamination, NO tearing. |
| 71 | HEP | dry | 10.57 | 1.040 | Delamination, NO tearing. |
| 72 | HEP | dry | 6.28 | 0.618 | Delamination, NO tearing. |
| 73 | HEP | dry | 8.11 | 0.798 | Delamination within HEP sheet. |
| 74 | HEP | water | 2.08 | 0.205 | Delamination, NO tearing. |
| 75 | HEP | water | 2.55 | 0.251 | Delamination, NO tearing, one corner of the samples slipped out of upper jaw. |
| 76 | HEP | water | 9.62 | 0.947 | Tore from edge. |
| 77 | HEP | water | 7.65 | 0.753 | Delamination, NO tearing. |

Conclusions Based on 34-5541 Results

Samples prepared with 34-5541, a hydrophobic hot melt adhesive varied in their wet and dry bond strengths according to the substrates used for testing. In general, the samples had less wet strength than dry strength. Despite the hydrophobic nature of the adhesive, this is to be expected because the carriers are typically weaker when wet. Considering the composites made with tissue in the machine direction, Examples 46–49 exhibited sufficient dry strength. Examples 57, 58 and 61 were all exemplary of the invention. They had sufficient wet strength, yet delaminated without tearing. Example 51 tore when wet, and was unacceptable. Examples 52–56, 59 and 60 all had sufficient wet strength, but exhibited some tearing of the wet carrier sheets. Accordingly, these latter examples were marginally representative of the invention. It is believed that the examples had localized regions of high adhesive add-on or had localized regions of weakness in the carrier sheets.

Considering the composites made with tissue in the cross direction, Examples 62–65 exhibited sufficient dry strength. Examples 66–69 tore when wet, and are not representative of the invention.

Considering the Examples made with HEP, Examples 70–73 exhibited sufficient dry strength. Examples 74, 75 and 77 are all exemplary of the invention; they had sufficient wet strength and delaminated without tearing. Example 76 had sufficient wet strength, but exhibited some tearing of the wet carrier sheets. Accordingly, these latter examples were marginally representative of the invention. It is believed that the examples may have been skewed in the jaws of the testing apparatus.

EXAMPLES 78–91

Peel Testing Results for Samples Bonded with 33-2058:

| Sample | Carrier | Condition | Force Newtons | Force per unit width N/cm | Mode of Failure |
|---|---|---|---|---|---|
| 78 | HEP | dry | 1.21 | 0.119 | Delamination, NO tearing. |
| 79 | HEP | dry | 0.35 | 0.034 | Delamination, NO tearing. |
| 80 | HEP | dry | 0.17 | 0.017 | Delamination, NO tearing. |
| 81 | HEP | dry | 1.00 | 0.098 | Delamination, NO tearing. |
| 82 | HEP | water | 0.46 | 0.045 | Delamination, NO tearing. |
| 83 | HEP | water | 0.30 | 0.030 | Delamination, NO tearing. |
| 84 | HEP | water | 0.29 | 0.029 | Delamination, NO tearing. |
| 85 | HEP | water | 0.56 | 0.055 | Delamination, NO tearing. |
| 86 | Machine | dry | 3.23 | 0.318 | Tear. |
| 87 | Machine | dry | 3.02 | 0.297 | Tear. |
| 88 | Machine | dry | 1.97 | 0.194 | Tear. |
| 89 | Machine | water | 1.46 | 0.144 | Delamination, |

-continued

Peel Testing Results for Samples Bonded with 33-2058:

| Sample | Carrier | Condition | Force Newtons | Force per unit width N/cm | Mode of Failure |
|---|---|---|---|---|---|
| 90 | Machine | water | 1.09 | 0.107 | slight tearing. Delamination, NO tearing. |
| 91 | Machine | water | 2.75 | 0.271 | Delamination, slight tearing. |

Conclusions Based on 33-2058 Results

Samples prepared with 33-2058 (poly vinyl acetate emulsion) adhesive varied in their wet and dry bond strengths according to the substrates used for testing. Additionally, significant variability in bond strength was observed among composites of the same composition. Among the composites made with the poly vinyl acetate emulsion, samples 78, 81, 82, 85, 86, 87, 88, 89, 90 and 91 exemplify the subject invention. Samples 79 and 80 had insufficient dry strength, while samples 83 and 84 had insufficient wet strength to be representative of the invention.

EXAMPLES 92–107

A suitable technique for determining the saturated free-swell volume of the high absorbency material within the absorbent laminate is the following Free-Swell procedure:

Five grams of high-absorbency material are sealed in a pouch which is sufficiently large that it will not inhibit the expansion of the contained and wetted high-absorbency material. The pouch material is a cellulose tissue having a basis weight of 21 gsm, has a wet strength which is sufficiently high to perform the test, and is porous to liquid. The pouch material substantially prevents the migration of the high-absorbency material out from the pouch, whether the high absorbency material is wet or dry. The cellulose tissue of the pouch is sealed at the edges with a bead of conventional, hot melt construction adhesive. The pouch containing the unrestrained high absorbency material is allowed to swell in an excess of a 0.85% saline solution for 15 minutes. The pouch containing the swollen high absorbency material is then pressed for 2.25 minutes under a pressure of 3.45 kPa and allowed to drain. The free swell capacity of the high absorbency material is the total grams of saline retained minus the wet weight of the pouch material, minus the dry weight of the high absorbency material, and then divided by the original dry weight (five grams) of the high absorbency material placed in the pouch (Free Swell value).

A technique for determining the saturated, expansion swelling of the high-absorbency material within an absorbent laminate is the following Laminate-Swell procedure:

The composite forming the absorbent laminate is sealed in a pouch, as described in the Free-Swell procedure. The pouch and absorbent composite contained therewithin are allowed to swell in excess 0.85% saline solution for 15 minutes. After the swelling period, the pouch and its contents are removed from the saline, placed under a pressure of 3.45 kPa and allowed to drain. The pouch is weighed to determine the total amount of fluid absorbed. The wet weight of the pouch, the wet weight of the absorbent laminate components (excluding the high absorbency material), and the dry weight of the high absorbency material are subtracted from the total wet weight of the combined pouch and contained absorbent laminate so that only the weight of the liquid contained by the high absorbency material is determined. The weight of liquid contained by the high absorbency material divided by the dry weight of the high absorbency material is the swelling capacity of the high absorbency material when assembled into the absorbent laminate (Laminate Swell value).

The wet weight of the pouch (Free-Swell procedure), or of the pouch containing all of the absorbent laminate components excluding the high absorbency material (Laminate Swell procedure) are determined by the same soaking procedure as described in those procedures (15 minute soak time followed by a drainage period of 2.25 minutes under an applied load of 3.45 kPa). The wet weights of these materials are used as tare weights in the calculation to determine the liquid contained by the high absorbency material.

Once all of the measurements have been taken in the Laminate Swell procedure, the pouch is carefully opened to examine the absorbent laminate. The absorbent laminate is examined and the number of pockets which ruptured (migrated superabsorbent due to the bursting of one of the absorbent laminate carrier layers) is recorded and expressed as a percentage of the total number of pockets in the absorbent laminate pattern.

The constriction of the swelling and absorption capacity of a polyacrylate superabsorbent material was determined for the following samples. The superabsorbent material was Favor SAB 870 available from Stockhausen, Inc., a business having offices in Greensboro, North Carolina. The absorbent laminate composites were prepared in accordance with the preparation procedure described for Examples 23–91 except that 17 gsm and 21 gsm cellulose tissues were used as the first carrier layer tissue and the sealing tissue respectively. The adhesive used in Examples 98–102 was Cycloflex 70-3998 (a hot melt, water sensitive adhesive) applied in a sprayed pattern at an add-on level of about 75 gsm. The adhesive used in Examples 103–107 was National Starch 34-5541 hot melt construction adhesive applied in a spray pattern at an add-on level of about 33 gsm. The samples prepared with the 34-5541 adhesive were annealed in a 60° C. convection oven for two minutes prior to testing to provide a good seal between the tissue layers.

| | | Absorbent Capacity Data | | | | |
|---|---|---|---|---|---|---|
| Example No. | Adhesive System | SAP Capacity (gm/gm) | % Capacity Change A | % Capacity Change B | % Torn | Delaminated (yes/no) |
| 92 | None | 29.1 | — | −7.6 | — | — |
| 93 | None | 26.5 | — | −15.9 | — | — |
| 94 | None | 25.6 | — | −18.7 | — | — |
| 95 | None | 28.4 | — | −9.8 | — | — |

-continued

| Example No. | Adhesive System | SAP Capacity (gm/gm) | % Capacity Change A | % Capacity Change B | % Torn | Delaminated (yes/no) |
|---|---|---|---|---|---|---|
| 96 | None | 29.4 | — | −6.7 | — | — |
| 97 | None | 29.1 | — | −7.6 | — | — |
| 98 | 70-3998 | 31.8 | 13.5 | — | 0 | yes |
| 99 | 70-3998 | 32.1 | 14.5 | — | 0 | yes |
| 100 | 70-3998 | 31.1 | 11.0 | — | 0 | yes |
| 101 | 70-3998 | 30.9 | 10.3 | — | 0 | yes |
| 102 | 70-3998 | 31.7 | 13.4 | — | 0 | yes |
| 103 | 34-5541 | 26.7 | −4.5 | −15.2 | 18.4 | no |
| 104 | 34-5541 | 28.0 | −0.1 | −11.1 | 10.5 | no |
| 105 | 34-5541 | 24.4 | −12.8 | −22.5 | 28.9 | no |
| 106 | 34-5541 | 26.7 | −4.5 | −15.2 | 36.8 | no |
| 107 | 34-5541 | 26.9 | −4.0 | −14.7 | 42.1 | no |

SAP = superabsorbent polymer
% Capacity Change A = determined with respect to the average of the SAP capacities of Examples 92-97 (Free-Swell).
% Capacity Change B = determined with respect to the average of the SAP capacities of Examples 98-102.
% Torn = Percentage of pocket regions in the laminate sample that had tears at least 3 mm in length.
gm/gm = grams of liquid absorbed per gram of SAP.

Examples 98–102 demonstrate the benefit of having the carrier layers delaminate to avoid excessive movement and excessive restriction of swelling of the high absorbency material contained within the discrete pockets.

Example Sets C, T, B and P

The Examples of Sample set C were prepared on the same vacuum box that was used to prepare Examples 23–91. A 17 gsm basis weight cellulose tissue was placed on the vacuum box. Then, 7 grams of Favor 870 superabsorbent were evenly distributed and brushed into the pockets formed in the cellulose tissue by the vacuum. Approximately 23 gsm of National Starch & Chemical Company Cycloflex 70-3998 adhesive were sprayed onto the tissue and superabsorbent using the PAM 600 Spraymatic Spray Gun set at 330° F. A second, 21 gsm cellulose tissue was then placed on top of the first tissue and the pocket sections of superabsorbent particles, and the spaces between and around the pockets were pressed by hand to obtain intimate contact between the tissue layers and the adhesive. The laminate structure was then trimmed to 140 mm×292 mm with a hand paper cutter.

The Examples of Sample set P were made with the same technique employed to produce the Examples of Sample set C except; a 102 mm×267 mm "window frame" template was placed over the first tissue to surround the area of the desired pocket array and to allow the Cycloflex adhesive to contact only the area inside the open "window" region of the template. After removing the template, the second tissue was superposed and applied onto the first tissue layer and the pockets of superabsorbent particles. Before removing the laminate from the vacuum box, the second tissue layer was folded back and approximately 23 gsm of National Starch and Chemical Company's 34-5541 adhesive was sprayed on the exposed edge using a second PAM 600 Spraymatic Spray Gun also set at 330° F. The folded back tissue was then unfolded and hand pressed into the adhesive to form the Secondary Attachment Means.

The Examples of Sample set B were made with the same technique employed to produce the Examples of Sample set P except; a 0.5–3 mm width line of 34-5541 adhesive was applied about 6 mm away from the edge of the pocket array on the exposed edge produced by folding back the second tissue layer. The adhesive line replaced the 23 gsm of sprayed adhesive employed for Sample set P.

The Examples of Sample set T were made with the same technique employed to produce the Examples of Sample set C except; 10 holes were blanked off to make a pocket array area of 87 mm×180 mm. 5.2 grams of the superabsorbent was used. 10 gsm Hydrofil® melt-blown was used in place of each layer of cellulose tissue. The laminate was trimmed to measure 140 mm×230 mm and was heat fused with a hand heat sealer 25 mm wide around the entire pocket array. The heat fused area was about 2 mm from the nearest pocket.

Gel Containment Test Method

To determine the ability of the secondary attachments to contain the superabsorbent, samples were soaked in excess (i.e. enough to submerge the samples) 0.85 weight percent saline for five minutes. Each sample was then lifted out of the saline on an open mesh polyolefin screen, shaken slightly to remove some of the excess liquid, placed on a lab bench and covered with a rigid piece of 152 mm×305 mm Plexiglass (i.e. of greater size than the pocket region 144). Weights were then placed on the Plexiglass to provide a uniformly distributed total pressure of 6.7 KPa (i.e. less weight was used for sample T since it was not as long). After five minutes, the weights and plexiglass were carefully removed. The total perimeter length of the secondary attachments was measured in millimeters.

Also measured was the length (in millimeters) of the portions of the secondary attachments along which exposed (escaped) superabsorbent was visible. The percentage of "open" perimeter was calculated by dividing the length of exposed superabsorbent by the total perimeter length of the secondary attachment means, and then multiplying the quotient by 100. The calculated percentage represents the Peripheral Release value.

Additional samples were made in accordance with procedures described above, except that the pockets of superabsorbent were eliminated. The secondary attachments were formed just by applying adhesive or by heat sealing to interconnect the two tissue layers. The resultant "lines" of attachment were then tested using the Delamination Testing Procedure (wet) described above. The results are summarized in the following table.

| Sample I.D. | % of Opened Attachment | Sample I.D. | Peak Wet Peel Strength of Secondary Attachments, N/cm |
|---|---|---|---|
| C-1 | 16.2 | C-12 | 0.086 |
| 2 | 8.8 | 13 | 0.086 |
| 3 | 12.4 | 14 | 0.086 |
| 4 | 7.5 | 15 | 0.089 |
| 5 | 9.4 | 16 | 0.085 |
| 6 | 11.8 | 17 | 0.129 |
| 7 | 13.2 | 18 | 0.093 |
| 8 | 21.0 | 19 | 0.078 |
| 9 | 5.0 | 20 | 0.077 |
| 10 | 0.0 | 21 | 0.053 |
| 11 | 8.0 | | |
| | avg = 10.3 | | avg = 0.086 |
| T-1 | 0 | T-7 | 0.282 |
| 2 | 0 | 8 | 0.373 |
| 3 | 0 | 9 | 0.144 |
| 4 | 0 | 10 | 0.057 |
| 5 | 0 | 11 | 0.110 |
| 6 | 0 | 12 | 0.132 |
| | avg = 0 | | avg = 0.186 |
| B-1 | 0 | B-7 | 0.195 |
| 2 | 0 | 8 | 0.230 |
| 3 | 0 | 9 | 0.210 |
| 4 | 3.8 | 10 | 0.220 |
| 5 | 0 | 11 | 0.202 |
| 6 | 0 | 12 | 0.196 |
| | | 13 | 0.232 |
| | avg = 0.6 | 14 | 0.146 |
| | | 15 | 0.197 |
| | | 16 | 0.211 |
| | | | avg = 0.213 |
| P-1 | 0 | P-7 | 0.060 |
| 2 | 0 | 8 | 0.170 |
| 3 | 0 | 9 | 0.181 |
| 4 | 0 | 10 | 0.124 |
| 5 | 0 | 11 | 0.102 |
| 6 | 0 | 12 | 0.181 |
| | | 13 | 0.147 |
| | avg = 0 | 14 | 0.124 |
| | | 15 | 0.101 |
| | | 16 | 0.124 |
| | | | avg = 0.134 |

These results indicate that the secondary attachments in Sample set C were not consistently acceptable. Samples T, B and P were consistently acceptable and are representative of the invention. These sample sets indicate the improved containment resulting from the higher Peak Wet Peel Strengths.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An absorbent article, comprising:
a first, liquid-permeable carrier layer and at least a second carrier layer;
water-sensitive attaching means for securing together said carrier layers at substantially attached first zones thereof, said carrier layers having substantially unattached zones providing a plurality of pocket regions with said substantially attached first zones located between said pocket regions;
high-absorbency material located within said pocket regions to provide an absorbent laminate; and
secondary attaching means for securing together said carrier layers along selected secondary attachment regions and providing a substantially water-insensitive connection therebetween, said secondary attachment regions substantially restricted to locations spaced from said pocket regions;
wherein, said water-sensitive attachment means in said substantially attached first zones provides a wet strength adequate to hold said carrier layers together when wet, and wherein said wet strength is less than a separating force imparted by a swelling of said high-absorbency material when said high-absorbency material is exposed to an aqueous liquid.

2. An absorbent article as recited in claim 1, wherein said secondary attaching means is substantially restricted to an outer periphery of said absorbent laminate.

3. An absorbent article as recited in claim 1, wherein said secondary attaching means is substantially restricted to an outer periphery of said absorbent laminate and interstitial locations between immediately adjacent pocket regions.

4. An absorbent article, as recited in claim 1, wherein said water-sensitive attachment means is configured to release at an applied load which is less than a load needed to delaminate said attachment means without excessively tearing at least one of said carrier layers when said carrier layers are wetted with an aqueous liquid.

5. An absorbent article, as recited in claim 1, wherein said water-sensitive attachment means provides a wet bond strength of not less than about 0.04N/cm.

6. An absorbent article, as recited in claim 5, wherein said water-sensitive attachment means provides a wet bond strength of not more than about 5N/cm.

7. An absorbent article, as recited in claim 1, wherein said water-sensitive attaching means provides a dry bond strength of at least about 0.05N/cm.

8. An absorbent article, as recited in claim 1, wherein said first carrier layer has a burst strength of at least about 0.08N/cm.

9. An absorbent article, as recited in claim 8, wherein said second carrier layer has a burst strength of at least about 0.08N/cm.

10. An absorbent article, as recited in claim 9, wherein said first carrier layer comprises a wettable fibrous web.

11. An absorbent article, as recited in claim 10, wherein said second carrier layer is liquid permeable and comprises a wettable, fibrous web.

12. An absorbent article, as recited in claim 11, wherein at least one of said carrier layers is a web which includes meltblown fibers and wherein said meltblown web is configured to provide water-sensitivity to said water-sensitive attaching means.

13. An absorbent article, as recited in claim 11, wherein at least one of said carrier layers is a high wet-strength tissue composed of cellulosic fibers.

14. An absorbent article as recited in claim 1, wherein said secondary attaching means includes lines of substantially water-insensitive attachment, said attachment lines having a width dimension of not more than about 3 cm.

15. An absorbent article as recited in claim 14, wherein said secondary attaching means includes lines of substantially water-insoluble adhesive.

16. An absorbent article as recited in claim 14, wherein said secondary attaching means includes lines of thermal bonds.

17. An absorbent article as recited in claim 14, wherein said water-sensitive attachment means provides a wet bond strength of not less than about 0.07N/cm.

18. An absorbent article as recited in claim 14, wherein said water-sensitive attachment means provides a wet bond strength of not less than about 0.09N/cm.

19. An absorbent article as recited in claim 18, wherein said water-sensitive attachment means provides a wet bond strength of not more than about 2N/cm.

20. An absorbent article as recited in claim 18, wherein said water-sensitive attachment means provides a wet bond strength of not more than about 1N/cm.

21. An absorbent article, as recited in claim 1, wherein said pocket regions are spaced apart from one another by a distance of not less than about 0.15 cm.

22. An absorbent article, as recited in claim 21, wherein immediately adjacent pocket regions are spaced apart from each other by a distance of not more than about 3 cm.

23. An absorbent article, as recited in claim 22, further comprising a surge management layer positioned generally adjacent a major bodyside surface of said absorbent laminate.

24. An absorbent article, as recited in claim 23, wherein said surge management layer is composed of a nonwoven fibrous web composed of synthetic fibers and having a basis weight within the range of about 24–300 gsm.

25. An absorbent article, as recited in claim 23, further comprising a distribution layer positioned next to a major outer side surface of said absorbent laminate.

26. An absorbent article, as recited in claim 23, wherein said distribution layer has a length which is within the range of about 75–175% of a corresponding length of said absorbent laminate.

27. An absorbent article, as recited in claim 26, wherein said distribution layer has a width which is within the range of about 75–175% of a corresponding width of said absorbent laminate.

* * * * *